United States Patent
Gonzalez Martinez et al.

(10) Patent No.: US 9,771,319 B2
(45) Date of Patent: Sep. 26, 2017

(54) CROSS-LINKER FOR THE PREPARATION OF A NEW FAMILY OF SINGLE ION CONDUCTION POLYMERS FOR ELECTROCHEMICAL DEVICES AND SUCH POLYMERS

(71) Applicant: Belenos Clean Power Holding AG, Biel/Bienne (CH)

(72) Inventors: Jose Antonio Gonzalez Martinez, Lausanne (CH); Monica Trincado Rodriguez-Pick, Zurich (CH); Hansjorg Friedrich Grutzmacher, Dielsdorf (CH)

(73) Assignee: Belenos Clean Power Holding AG, Biel/Bienne (CH)

( * ) Notice: Subject to any disclaimer, the term of this patent is extended or adjusted under 35 U.S.C. 154(b) by 0 days.

(21) Appl. No.: 14/955,264

(22) Filed: Dec. 1, 2015

(65) Prior Publication Data
US 2016/0168086 A1    Jun. 16, 2016

(30) Foreign Application Priority Data
Dec. 10, 2014    (EP) .................................... 14197209

(51) Int. Cl.
*C07C 311/15*    (2006.01)
*C07C 311/48*    (2006.01)
(Continued)

(52) U.S. Cl.
CPC .......... *C07C 311/15* (2013.01); *C07C 311/48* (2013.01); *C08F 212/14* (2013.01);
(Continued)

(58) Field of Classification Search
CPC .......... H01M 10/0525; H01M 10/054; H01M 10/0565; H01M 10/0568; H01M 4/0402;
(Continued)

(56) References Cited

U.S. PATENT DOCUMENTS 5,837,400 A    11/1998    Baudry et al.

FOREIGN PATENT DOCUMENTS

WO    WO 2013/034848 A1    3/2013

OTHER PUBLICATIONS

European Search Report issued May 26, 2015 in European Application 14197209, filed on Dec. 10, 2014.
(Continued)

*Primary Examiner* — Jane Rhee
(74) *Attorney, Agent, or Firm* — Oblon, McClelland, Maier & Neustadt, L.L.P.

(57) ABSTRACT

A specific cross-linker, an alkaline metal bis(styrenesulfonyl)imide monomer, is used in the synthesis of single ionic conductive copolymers that are non-fluorinated and non-PEO based. Such copolymers meet the security and costs requirements to be used as solid polymers electrolytes (SPE). They are promising alternatives to standard liquid electrolytes in alkaline metal-ion batteries because of their improved security and inflammability properties. The copolymers described are either polyvinylsulfonates or acrylate vinylsulfonate block-copolymers. Preferred acrylate monomers are methacrylates and preferred vinylsulfonates are styrene sulfonates. The copolymer is prepared by radical polymerization of the vinyl sulfonate and the cross-linker and optionally the acrylate, in particular radical photopolymerization using a functionalized bis(acyl)phosphane oxide (BAPO) as photoinitiator. Also described is the use of such copolymer as solid polymer electrolyte in a lithium ion battery.

34 Claims, 9 Drawing Sheets

(51) Int. Cl.
| | |
|---|---|
| *H01M 10/0525* | (2010.01) |
| *H01M 10/054* | (2010.01) |
| *H01M 10/0565* | (2010.01) |
| *H01M 10/0568* | (2010.01) |
| *C08F 212/14* | (2006.01) |
| *C08F 220/14* | (2006.01) |
| *H01M 4/04* | (2006.01) |
| *H01M 4/13* | (2010.01) |
| *H01M 4/139* | (2010.01) |
| *H01M 4/36* | (2006.01) |
| *H01M 4/62* | (2006.01) |
| *H01M 4/02* | (2006.01) |

(52) U.S. Cl.
CPC ......... *C08F 220/14* (2013.01); *H01M 4/0402* (2013.01); *H01M 4/0483* (2013.01); *H01M 4/13* (2013.01); *H01M 4/139* (2013.01); *H01M 4/364* (2013.01); *H01M 4/625* (2013.01); *H01M 10/054* (2013.01); *H01M 10/0525* (2013.01); *H01M 10/0565* (2013.01); *H01M 10/0568* (2013.01); *H01M 2004/027* (2013.01); *H01M 2004/028* (2013.01); *H01M 2300/0082* (2013.01)

(58) Field of Classification Search
CPC ...... H01M 4/0483; H01M 4/13; H01M 4/139; H01M 4/364; H01M 4/625; H01M 2300/0082; H01M 2004/027; H01M 2004/028

See application file for complete search history.

(56) References Cited

OTHER PUBLICATIONS

Bahar Azimipour et al. "Radical copolymerization of potassium 4-vinyl biphenyl-sulfonylimide and oligo (oxyethylene) methacrylates. Thermal behavior and single-ion conductivity of the copolymer electrolytes formed", Polymer Bulletin, vol. 49, No. 4, 2002, 9 pages.

Rachid Meziane et al. "Single-ion polymer electrolytes based on a delocalized polyanion for lithium batteries", Electrochimica Acta, vol. 57, 2011, 6 pages.

Jeff Tollefson "Charging up the Future", Nature 2008, 5 pages.

Fangyi Cheng et al. "Functional Materials for Rechargeable Batteries", Advanced Materials 2011, 21 pages.

M. Armand et al. "Building Better Batteries", Nature, vol. 451, 2008, 6 pages.

Peter G. Bruce et al. "Li—$O_2$ and Li—S Batteries with high energy storage", Nature Materials, vol. 11, 2012, 12 pages.

A.Hammami et al. "Runaway risk of forming toxic compounds", Nature 2003, 3 pages.

Kazuo Murata et al. "An overview of the research and development of solid polymer electrolyte batteries", Electrochimica Acta 45, 2000, 8 pages.

P.G. Bruce et al. "Polymer Electrolytes", J. Chem. Soc. vol. 89, 1993, 17 pages.

M. Marzantowicz et al. "Influence of Crystalline complexes on electrical properties of PEO:LiTFSI electrolyte", Electrochimica Acta 53, 2007, 9 pages.

Richard Vaia et al. "New Polymer Electrolyte Nanocomposites: Melt Intercalation of Poly(ethylene Oxide), in Mica-type Silicates", Advanced Materials, 1995, 3 pages.

Shan Wong et al. "What do NMR linewidth tell us? Dynamics of alkali cations in a PEO-based nanocomposite polymer electrolyte", Electrochimica Acta vol. 42, 1997, 6 pages.

Juraj Bujdak et al "Effect of Layer Charge on the Intercalation of Poly(ethylene oxide) in Layered Silicates: Implications in Nanocomposite Polymer Electrolytes", Chem Mater, 2000, 7 pages.

C. Capiglia et al. "Effects of nanoscale $SiO_2$ on the thermal and transport properties of solvent-free, poly(ethylene oxide) (PEO)-based polymer electrolytes", Solid-State Ionics, 118, 1999, 7 pages.

F. Croce et al. "Nanocomposite polymer electrolytes for lithium batteries", Letters to Nature, 1998, 3 pages.

M. Forsyth et al. "The effect of nano-particle $TiO_2$ fillers on structure and transport in polymer electrolytes", Solid State Ionics, 147, 2002, 9 pages.

Asghar Aryanfar et al. Dynamics of Lithium Dendrite Growth and Inhibition: Pulse Charging Experiments and Monte Carlo Calculation, The Journal of Physical Chemistry Letters, 2014, 6 pages.

(a) L1  (b) L1-pressed (c) L2  (d) L2-pressed

CROSS-LINKER FOR THE PREPARATION OF A NEW FAMILY OF SINGLE ION CONDUCTION POLYMERS FOR ELECTROCHEMICAL DEVICES AND SUCH POLYMERS

This application claims priority from European Patent Application No. 14197209.1 filed Dec. 10, 2014, the entire disclosure of which is incorporated herein by reference.

TECHNICAL FIELD

The present invention concerns cross-linkers suitable for being used in the production of conducting copolymers that are suitable for being used in lithium ion batteries as well as such copolymers.

BACKGROUND ART

The development of fully electric or hybrid vehicles has become an urgent need for sustainable long-term development.[1] The most important challenge in the near future is to find a safe, cheap and efficient battery technology that would provide electric vehicles with an extended driving range (>300 km). The corresponding increase in energy density requires the development of new chemistries for both the active electrode materials and the electrolyte.[2] Lithium metal is the ultimate anode and the only choice to complement the positive air ($O_2$) or sulfur cathodes and to take advantage of the high specific capacities of these cathodes.[3] Nevertheless, the use of lithium metal in contact with a liquid electrolyte leads to important safety problems associated with the formation of irregular metallic lithium electrodeposits during the recharge. This would result in dendrite formation responsible for explosion hazards. To meet the requirements of the electric vehicle mass market, the Li ion batteries must improve the safety issues related to the thermal instability,[4] with formation of flammable reaction products, the possibility of leaks, and internal short-circuits. Solid-state electrolytes are the perfect solution to mitigate the lithium dendritic growth.[5] The use of a solid polymer electrolyte (SPE), where a lithium salt is associated with a polar polymer matrix, can solve most of the safety issues mentioned above. Moreover, other advantages related to the battery processing, as the lamination (Li metal, electrolyte, composite, cathode), stacking and hermetic sealing would be easier and cost-effective with a polymer electrolyte.

During the past 50 years, many polymer/lithium salt systems have been considered as replacement of liquid electrolytes in Li-ion batteries. The difficulty for the development of a suitable polymeric material resides in the ability to design a polymer that merges a high ionic conductivity and good mechanical properties.[6] The most widely studied and used systems are based in fluorinated salts dissolved in an aprotic polymer matrix of polyethylene oxide (PEO), which contains ether coordination sites that enable the dissociation of salts, together with a flexible macromolecular structure that assists ionic transport. Nevertheless, the presence of PEO crystalline regions interferes with ion transport, which requires an amorphous phase.[7] At high temperatures, above 65° C., most of the PEO based polymers become a viscous liquid and lose their dimensional stability.[8] Moreover, in the PEO-fluorinated salts systems the motion of lithium ions carries only a small fraction (⅕th) of the overall ionic current, which leads, during battery operation, to the formation of a strong concentration gradient favoring dendritic growth, which limits the power delivery.[9] For this reason, single ion polymers are preferred wherein $Li^+$ migration is alone responsible for the ionic conduction of polymer.

In the last years, blending different types of polymers or direct copolymerization have been broadly used to match the requirements in terms of ionic conductivity and mechanical properties of SPE polymers. The advantage of a copolymer approach is the possibility of tailoring the mechanical properties as the rigidity/malleability by functionalization of the building blocks, which might include a new polymeric unit. By combining different functional units, the lithium conductivity and the electrochemical stability against alkaline metals can be improved. The mobility of the polymer chains can be enhanced by combining the copolymer with a plasticizer to avoid dense packing of the polymer and crystallization.

Up to now, however, conducting polymers that meet the mechanical and conductivity demands have not yet been provided to satisfaction. Therefore it is the goal of the present invention to provide monomers, monomer compositions and single-ion solid copolymer electrolytes with improved conductivity and/or mechanical properties.

DISCLOSURE OF THE INVENTION

Hence, it is a general object of the invention to provide a cross-linker suitable as comonomer in the production of single-ion solid copolymer electrolytes.

Now, in order to implement these and still further objects of the invention, which will become more readily apparent as the description proceeds, the cross linker is manifested by the features that it is a bis(styrylsulfonylimide) alkaline metal salt, i.e. the compound of formula (I) as below

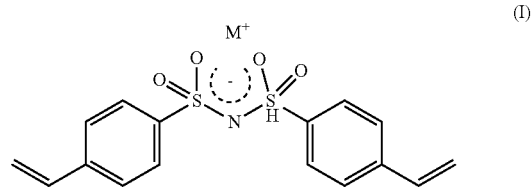

(I)

wherein $M^+$ is $Li^+$ or $Na^+$.

A presently preferred salt is the lithium salt.

This cross-linker is especially suitable for use in the preparation of single ion conduction polymers (also termed (single-ion) conducting (co)polymers or (single-ion) conductor (co)polymers) or, if used for application in batteries, (single-ion) conducting (solid) electrolyte or merely solid electrolyte).

In the production of single-ion solid copolymer electrolytes any radical initiator can be used, i.e. thermally activated and UV activated radical initiators and mixtures of thermally activated and UV activated radical initiators. Such thermally activated and/or UV activated initiators are able to form one or preferably two radicals.

Suitable photoinitiators include α-hydroxyketones, benzophenones, benzyl derivatives, thioxanthones, acetylphosphanes or especially acylphosphane oxides. Acetylphosphanes and in particular acetylphosphane oxides allow high curing speeds at higher material depths. Presently preferred are photoinitiators of the acetylphosphane type or acylphosphane oxide type as they are e.g. described in WO 2006/056541, WO 2011/003772 and WO 2014/053455. These documents are incorporated herein by reference in their entirety.

The general structure of acylphosphane oxide type photoinitiators is represented by formula (II) below:

$$R^1 {-} \left[ \begin{array}{c} R^3_{(2-m)} \quad O \\ | \quad\quad \| \\ P {-\!\!-\!\!-\!\!-} [{-\!\!-} R^2]_m \\ \| \\ X \end{array} \right]_n \quad \text{(II)}$$

In such photoinitiators:
n is from 1 to 6, preferably n is equal to 1, 2, 3 or 4, and more preferably 1 or 2,
m is 1 or 2,
X is oxygen or sulfur,
$R^1$ is —$C(R^4)_3$, wherein
  if n=1,
  all $R^4$ are independently from each other selected from the group consisting of
    H
    aromatic groups,
    alkenyl groups and
    aliphatic groups, wherein the aliphatic groups can be unbranched or branched, non-substituted or substituted by one or more of the following groups: aromatic groups, heteroaromatic groups, heterocyclic groups, ethers (polyethyleneglycol or polyethylene oxide), selenides, hydroxyl, thiol, ketones, imines, carboxylic acid derivatives, sulfones, sulfoxides, sulfates, sulfonium, sulfimines, sulfoximine, sulfonamide, amine, ammonium salts, nitriles, nitro, amidines, carbamates, guanidinium, hydrazones, hydrazides, hydrazines, silanes, siloxanes, polysiloxanes, phosphonium, phosphinates, phosphine oxide or phosphate groups.
  if n>1, in particular n is from 2 to 6, preferably n is 2, 3 or 4, at least one $R^4$ is a 2 to 6-valent substituent selected from the list described above, wherein the afore mentioned alkyl can also comprise one, two or more of the afore mentioned groups within the chain, i.e. the aliphatic chain may be once, twice or more times interrupted (or interconnected) by functional groups previously mentioned, or be substituted once or more times with such groups, wherein said groups are non-successive, i.e. separated by at least one $CH_2$-group
$R^2$ is an aryl group, preferably 2,4,6-trimethylphenyl (mesityl) or 2,6-dimethoxyphenyl, and
$R^3$ is —$C(R^4)_3$ as specified above for R1.

Such photoinitiators can be used in combination with photoinitiators of the same class and/or in combination with photoinitiators of other class(es). Preferred initiators are bis(acyl)phosphane oxides (BAPOs). Such BAPOs can e.g. be used together with initiators that can complement the curing properties of the BAPOs, such as α-hydroxyketones, benzophenones, benzyl derivatives, thioxanthones, or other acylphosphane oxides.

In presently preferred embodiments, the radical initiator is a photoinitiator suitable to generate two radicals, in particular a photoinitiator of formula (II) above wherein:
n is 1,
m is 2,
X is O
$R^1$ is —$CH_2$—$CH_2(Z)$,
Z is —$(CH2)_{n_1}$-$NMe_3X'^+$, wherein $n_1$ is from 1 to 4, more preferably 1 to 3 and X' is Cl, Br, or I, preferentially Br Z is an ester —$(CO)OR^6$ wherein
$R^6$ is an alkyl comprising within its chain or said alkyl chain being interrupted by one or more —O— (like a polyethylene group), or carrying one or more siloxy groups such as —$SiR^7_y(OR^8)_{3-y}$, wherein y is from 0 to 3, or carrying one or more ammonium salt groups such as —$N(R^9)^{4+}X'^-$, X' being as defined above, wherein
$R^7$, $R^8$ and $R^9$ are alkyl groups, preferably $C_1$ to $C_4$ alkyl groups, and
$R^2$ is a mesityl group or a 2,6-dimethoxyphenyl group, more preferred a mesityl group or
n is 2,
m is 2,
R1 is —$(CO)O$—$(CH_2$—$CH_2$—$O)_x$—$O(CO)$— wherein x is in the range of 1 to 1000, preferably from 1 to 100, most preferred x is about 100
$R^2$ is a mesityl group or a 2,6-dimethoxyphenyl group, more preferred a mesityl group.

These photoinitiators will further be termed BAPO (for bis(acyl)phosphane oxide).

The synthesis of the BAPO photo-initiators (BAPO-1 and derivatives BAPO-2, BAPO-3, BAPO-4 and BAPO-5 and BAPO-6) are available through patents PCT/EP2013/070378 (WO 2014/053455), WO 2006/056541 and WO 2011/003772.

As already indicated above, presently preferred photoinitiators used within this invention include either $R^1$ being small functional groups (BAPO-1 BAPO-3 and BAPO-6) or grafted polymers (BAPO-4 and BAPO-5). BAPO-4 is a photoinitiator functionalized with a polysiloxane macromolecule (e.g. obtainable by polymerizing BAPO-2) with a Mn of up to about 2400 such as 2136 for the BAPO-4 used herein. BAPO-5 is functionalized with a polyethyleneoxide (PEO, Mn 6000) bonded at a phosphorous atom at each end (n=2). The nature of the BAPO can influence the final polymer not only via the side chains attached but also via its polymerization activity, leading to polymers with different mechanical and conducting properties. In the following formulas, Mes is mesitylene or 1,3,5-trimethylbenzene, respectively.

BAPO-1

BAPO-2

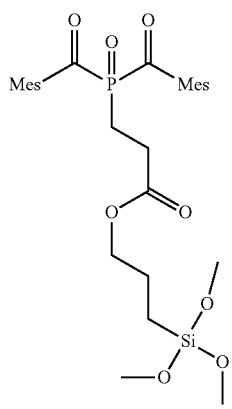

BAPO-3

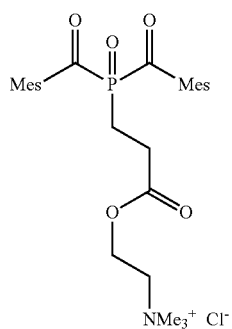

BAPO-4

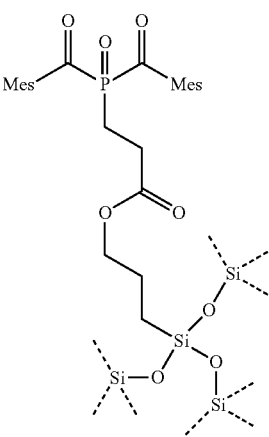

BAPO 5

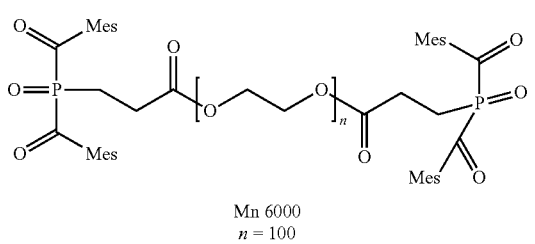

Mn 6000
n = 100

BAPO-6

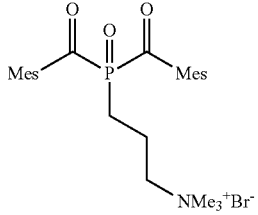

Dependent on the one or more radical initiator chosen, the cross-linker of the present invention can be used together with a vinyl sulfonate monomer, preferably styrene sulfonate monomer, alone or together with an acrylate monomer to form a copolymer (CP) that—in case that acrylate monomer is added—is also called a tri-block copolymer (TBP) or—in the absence of acrylate di-block-copolymer (DBP). For lithium-ion batteries the preferred alkaline metal is lithium, for sodium batteries sodium.

Using the cross-linker and a suitable radical initiator as those described above, non-fluorinated single-ion copolymer electrolytes can be prepared, optionally using an acrylate as further comonomer, preferably a methacrylate such as an alkylacrylate, e.g. methylmethacrylate. As a further comonomer an alkaline metal sulfonate vinyl monomer is used, preferably an alkaline metal styrene sulfonate monomer wherein the alkaline metal is sodium or lithium.

Copolymers of methacrylate, the linker and a lithium styrene sulfonate monomer, prepared using one of BAPO-1 to BAPO-5 were found to be thermally stable up to above 190° C. and offering a single-ion conductivity in the range of $10^{-4}$ S cm$^{-1}$ at 60° C., i.e. one order of magnitude superior to the state of the art in single-ion polymer electrolytes[10].

As already mentioned above, the non-fluorinated single-ion conduction copolymer electrolytes comprising (meth)acrylates are also termed tri-block polymers (TBP) although their actual structure cannot be determined due to lacking solubility. Thus, that the inventive copolymer electrolytes might be tri-block copolymers is a mere assumption based the fact that acrylates like methacrylates are known for fast homopolymerization and on the solid content and isolated yield of the obtained polymer. Nevertheless, the invention shall not be limited in any way by this assumption or this terminology.

In analogy to TBPs copolymers of vinyl sulfonate monomers and cross-linker are termed di-block (co)polymers (DBP) since—due to the difference in molar ratios—at least blocks of polyvinylsulfonates are present.

The copolymer (TBP) is suitably formed by a radical initiator (in particular a photoinitiator such as a BAPO) with promoted polymerization of an acrylate, preferably a methacrylate, in particular methylmethacrylate, an alkaline metal vinyl sulfonate monomer, preferably a styrene sulfonate like lithium styrene sulfonate and a bifunctional vinyl monomer linker, i.e. the alkaline metal (bis(styrenesulfonyl)imide), like lithium(bis(styrenesulfonyl)imide) in aqueous media. The general structure of a resulting tri-block or di-block copolymer obtained by using one of BAPO 1-6 and preferred monomers is shown below.

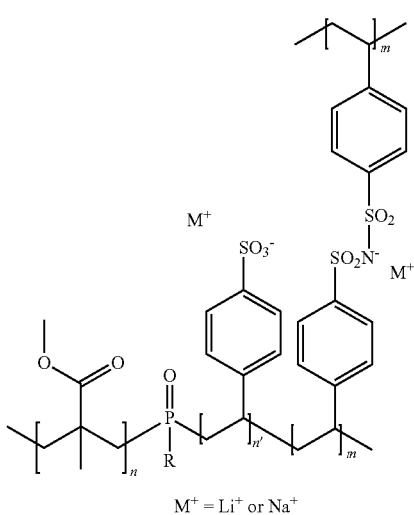

$M^+ = Li^+$ or $Na^+$

Polymer CP-1 or TBP-1: R=—CH$_2$CH$_2$CO(OCH$_2$CH$_2$)$_2$OCH$_2$CH$_3$
Polymer CP-2 or TBP-2: R=—CH$_2$CH$_2$CO$_2$(CH$_2$)$_3$Si(OCH$_3$)$_3$
Polymer CP-3 or TBP-3: R=—CH$_2$CH$_2$CO$_2$(CH$_2$)$_2$NMe$_3^+$Br$^-$
Polymer CP-4 or TBP-4: R=—CH$_2$CH$_2$CO$_2$(CH$_2$)$_3$SiO$_3$—
Polymer CP-5 or TBP-5: R=—CH$_2$CH$_2$CO(OCH$_2$CH$_2$)$_n$O$_2$COCH$_2$CH$_2$—
Polymer CP-6 or DBP-6 (n=0): R=—CH$_2$CH$_2$CH$_2$N(CH$_3$)$_3$Br Dependent on the desired features, the monomer ratios can be varied within certain ranges. The sulfonyl groups are needed for conductivity while in certain embodiments, dependent on the photoinitiator used, a (meth)acrylate is needed for mechanical stability. Taking these demands in consideration, the ratio of vinyl sulfonate monomer to acrylate monomer is 1:0 to 1:4. The cross linking monomer can be present in a ratio of up to 20 mol % referred to the amount of the other monomers, i.e. the acrylate monomers and the vinyl sulfonate monomers, and preferably is present in amounts of about 10 mol %.

In specific embodiments, in particular if BAPOs are used that comprise an ester group in R1 like BAPO-1 to BAPO-5, the ratio of alkaline metal vinyl sulfonate monomer:acrylate monomer can be varied from about 1:4 to about 4:1 (or the other way round the acrylate monomer:alkaline metal sulfonate vinyl monomer can be varied from about 4:1 to about 1:4) with a ratio of about 1:1 being presently preferred. Therefore, in a presently preferred embodiment a molar ratio of (meth)acrylate groups to sulfonate groups is about 1 and preferably the ratio of (meth)acrylate:vinyl sulfonate:bis(styrenesulfonyl)imide is about 1:1:0.2.

For other BAPOs like BAPO-6, the acrylate may not be needed. For such polymers the ratio of vinyl sulfonate:(bis(styrenesulfonyl)imide can be varied from 10:2 to 10:0.5, wherein 10:1 is preferred.

The optimal amount of radical initiator can easily be determined by concentration series. However, the photoinitiator and/or thermally induced initiator usually is present in about 1 mol % of total monomers, i.e. (meth)acrylate and vinyl sulfonate and bis(styrenesulfonyl)imide.

The final cross-linked polymer network structure facilitates weak interactions of M$^+$ with this anionic structure, offering a high dissociation level and alkaline metal ion-mobility through the matrix (for Li $10^{-4}$ S cm$^{-1}$ at 60° C.). The result of the polymerization with BAPO-1 to -5 is an emulsion of polymer particles of 80-200 nm size. The result of the polymerization with BAPO-6 is a water-soluble ion conducting polymer.

During the reaction an alkaline metal containing surfactant (e.g. lithium dodecylsulfate) may be added that allows an effective control over the particle size and stability of the final emulsion, with a particle size distribution stable for several weeks.

A bis(acyl)phosphane oxide linked to an inorganic material such as a metal oxide (see FIG. 1). The aim of using such coupled initiator in the preparation of a single-ion conduction polymer is to achieve an intimate contact between a lithium ion or sodium ion active material and a Li-ion or Na-ion conductor polymer. As a proof of concept, the polymerization of MMA (methyl methacrylate) with BAPO linked to a vanadate in an organic solvent is described below.

A siloxane group containing BAPO such as BAPO-2, can be anchored to a material such as an electronically active material like a vanadate by co-suspending the reagents in a suitable organic solvent like THF and refluxing for an appropriate time in inert gas such as 4 h in argon.

The invention also relates to a drying process that allows processing the SPE emulsion to end with a SPE self-standing film. An electrochemical cell can be formed by positioning this SPE self-standing film between an anode and a cathode, said SPE self-standing film working as a separator. The invention also covers the direct deposition of SPE by solution casting on the electrode.

It is also within the scope of the present invention to add a plasticizer. Dependent on the time of addition and the amount or ratio, respectively, the features of the polymer film can be varied. In general a minimum of 5 and a maximum of 20 wt % of plasticizer such as tetraethyleneglycol dimethylether (TEG) might be used in a SPE separator.

In a further aspect this invention relates to an alkaline metal-ion battery like a lithium-ion battery where a SPE film separates a negative electrode made of metallic lithium and a positive electrode, prepared by mixing a cathodic active material (for example LiFePO$_4$ or Li$_x$H$_y$V$_3$O$_8$ wherein in this formula $2<x+y<6.8$ and $0<x<4$ and $0.5<y<6$) or a composite vanadate/graphene material as described in EP 2 755 259 (A1) "Self-assembled composite of graphene oxide and H4V3O8") with conductive carbon additives and the SPE described above. In this configuration the SPE plays two roles, namely as a separator and as an electrolyte.

In such an embodiment, the SPE used for mixing with the cathode material and conductive carbon may have low mechanical strength but high conductivity and the self-standing film may have lower conductivity but improved mechanical stability.

In another embodiment, the SPE emulsion can optionally be admixed with an inorganic filler like fumed silica, titanium oxide, aluminum oxide, zirconium oxide, boron oxide, etc. Such inorganic nanosized fillers are in particular used to improve mechanical features of self-standing SPE films.

In another method, the active cathode material and conductive carbon is coated or mixed with the monomers and the initiator and then polymerization is initiated or—in an alternative method—the initiator is attached to the active cathode material and then combined with the monomers prior to polymerization initiation. Due to diffusion of the monomers into the porous cathodic material and conductive carbon layer, use of a thermally activated initiator instead of a photoinitiator may be advantageous. Also in this embodiment the application of a SPE self standing film as (additional) separator may be needed.

It is also possible to use a two-step method, i.e. to first produce a cathode using usual binder or SPE if need be for obtaining a sufficiently stable cathode, and then coating this cathode with an SPE layer. Due to the intimate contact of the SPE layer with the cathode layer, the stability of the SPE layer is improved in comparison with a separately produced and then applied self-standing layer.

By changing the composition of the monomers and the fillers the features of the copolymer can be varied and to a large extent adapted to the specific needs with regard to conductivity and mechanical properties. As indicated above, it is also possible and often preferred to use combinations of SPEs, e.g. one layer of high conductivity and poorer mechanical strength with a self-standing film of lower conductivity.

The advantage of using a SPE layer or a self-standing film is an improved prevention of dendrite formation.

The composite films made of the SPE conducting polymer and the active cathode material are designed to assure an optimal interface between the electrode and the SPE-separator, providing an additional advantage when designing a full battery cell. Besides a good mechanical contact between the layers, the electrolyte polymer can also enhance local ion conduction inside the electrode.

The SPE of the present invention cannot only be admixed with cathode material but also with anode material. The above comments apply respectively. Nevertheless, the much preferred anodes at present are metallic lithium or sodium.

The electrochemical stability versus lithium and electrochemical feasibility has been shown using standard cathodes materials, such as lithium iron phosphate (LFP), or novel active materials, such as lithium vanadates, which is a highly attractive cathode material for the next generation of Li-ion batteries as e.g. described in EP 2 755 259 A1. The tri-block polymeric single ion conductor (denoted as TBP) can suitably be synthetized by a radical polymerization triggered by photo-initiators in water.

Therefore, besides of the specific linker and the therewith produced solid conducting polymers, other aspects of the present invention are electrodes comprising active electrode material, SPE and possibly conducting fillers like graphene, graphite, conducting carbon and combinations thereof, as well as batteries produced using an SPE of the present invention as electrolyte, preferably in combination with a metal anode. Such a battery can be produced by a method comprising the step of coating a releasable support such as an aluminum foil with active electrode material and optionally conductive fillers to form a cathode and then coating the cathode with a coating of a solid conducting polymer of the present invention.

BRIEF DESCRIPTION OF THE DRAWINGS

The invention will be better understood and objects other than those set forth above will become apparent when consideration is given to the following detailed description thereof. This description makes reference to the annexed drawings, wherein.

MODES FOR CARRYING OUT THE INVENTION

Figure 1:
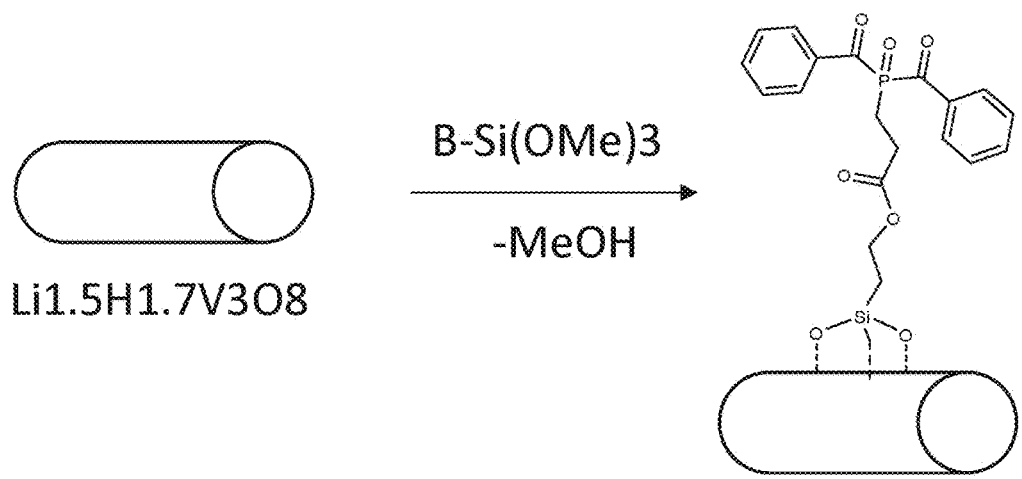
FIG. 1: Synthesis of photoinitiator BAPO-Vanadate

As indicated above, the present invention relates to cross-linkers suitable in the synthesis of single ionic conductive copolymers that are non-fluorinated and non-PEO based. Such copolymers meet the security and costs requirements to be used as solid polymers electrolytes (SPE). They are promising alternatives to standard liquid electrolytes in the Li-ion batteries or Na-ion batteries because of their improved security and inflammability properties. The copolymers described are either polyvinylsulfonates or polyacrylates, in particular methacrylates such as polymethylmethacrylates (PMMA) functionalized with alkaline metal polyvinylsulfonyl like alkaline metal polysulfonylstyrene such as lithium polysulfonylstyrene (LiPSS) and crosslinked by the use of the inventive linker, i.e. the alkaline metal (like Li) bis(styrenesulfonyl)imide (MBSSI like LiBSSI) monomer. The copolymers of the present invention can be prepared by radical polymerization, in particular radical photopolymerization, preferably photopolymerization using a functionalized bis(acyl)phosphane oxide (BAPO) as photoinitiator. Such copolymers can be used as solid polymer electrolytes in lithium-ion or sodium-ion batteries.

Experimental Section

1) Commercial Starting Materials

Lithium styrene sulfonate was purchased from Tosoh Europe B.V., The Netherlands (>94%) and was purified before usage by recrystallization from bis(2methoxyethyl) ether (DME) and dried under vacuum at 100° C. for 2 days.

Methyl metacrylate (MMA) was purchased from Aldrich (>99%) and was distilled prior to use. Tetraethyleneglycol dimethyl ether (TEG) was purified by distillation and stored over molecular sieves.

2) Synthesis of the Cross Linker: Bis(Styrylsulfonylimide) Lithium Salt

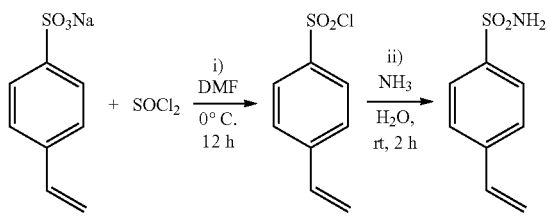

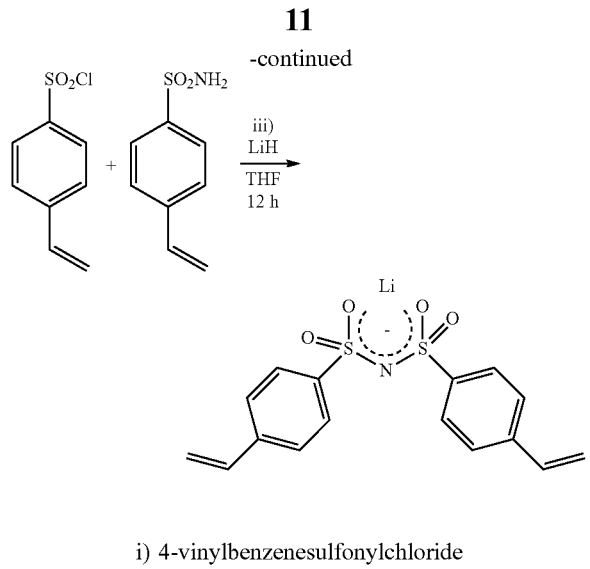

i) 4-vinylbenzenesulfonylchloride

A solution of 4-vinylbenzenesulfonic acid sodium salt (7.2 g, 35 mmol, 1 eq) in dimethylformamide (DMF) (58 mL) was cooled to 0° C. before adding thionyl chloride (34.4 g, 21 mL, 289 mmol, 8.3 eq) dropwise. The thionylchloride was degassed but used without purification. After stirring for 12 h, the mixture was left at −4° C. overnight and then poured into ice-water (100 mL) and extracted with diethylether (3×50 mL). The solution was concentrated under reduced pressure affording a yellowish oil (4.4 g, 66%).

$^1$H-NMR (500.2 MHz, CDCl$_3$) δ=7.92 (d, J=8.0 Hz, 2H, CHAr), 7.56 (d, J=7.5 Hz, 2H, CHAr), 6.81 (m, 1H, CHolef), 5.92 (d, J=17.5 Hz, 1H, CHolef), 5.47 (d, J=11.0 Hz, 1H, CHolef) ppm.

$^{13}$C{$^1$H}NMR (75.5 MHz, CDCl$_3$): δ=144.9 (CH$_2$=CH—C), 142.9 (CSO$_2$Cl), 135.0 (CH$_2$=CH), 127.6 (CHAr), 127.2 (CHAr), 119.5 (CH$_2$) ppm.

ii) 4-Vinylbenzenesulfonylamide 4-vinylbenzenesulfonylchloride (2 g, 9.87 mmol, 1 equiv) was reacted for 2 h with aqueous ammonia solution (100 mL, (25% NH$_3$)) and then extracted with ether, dried over MgSO$_4$ and concentrated giving the sulfonamide as a white solid (1.11 g, 62%).

Mp:141° C.

$^1$H-NMR (500.2 MHz, CDCl3): δ=7.95 (d, J=8.0 Hz, 2H, CHAr), 7.58 (d, J=8.5 Hz, 2H, CHAr), 6.75 (m, 1H, CHolef), 5.94 (d, J=17.5 Hz, 1H, CHolef), 5.50 (d, J=11.0 Hz, 1H, CHolef), 3.08 (s, 2H, NH$_2$) ppm.

iii) Bis(styrylsulfonylimide) lithium Salt

A mixture of 4-vinylbenzenesulfonylchloride (323 mg, 1.6 mmol, 1 eq), 4-vinylbenzenesulfonylamide (293 mg, 1.6 mmol, 1 eq) and LiH (77 mg, 3.2 mmol, 2 eq) in THF (5 mL) was stirred for 12 h under Ar at room temperature, then concentrated and washed with ether giving a white solid. The solid was recrystallized from MeOH affording 0.4 g, 71% yield.

Mp: >250° C. dec.

$^1$H-NMR (500.2 MHz, D$_2$O): δ=7.61 (m, 4H, CHAr), 7.46 (m, 4H, CHAr), 6.76 (m, 2H, CHolef), 5.91 (d, J=17.5 Hz, 2H, CHolef), 5.36 (d, J=11.0 Hz, 2H, CHolef).

$^{13}$C-NMR (75.5 MHz, D$_2$O): δ=141.9 (CH$_2$=CH—C), 138.9 (CSO$_2$N), 135.4 (CH$_2$=CH), 126.7 (CHAr), 125.8 (CHAr), 116.4 (CH$_2$) ppm.

$^7$Li-MAS NMR δ=0 ppm

ATR IR: $λ^{-1}$ (cm$^{-1}$)=1626 w, 1494 m, 1424 m, 1200 s, 1137 m, 1093 s, 989 s, 904 m, 839 s, 743 m.

EA Calc: C, 54.0%; H, 4.0%. Found C, 53.4%; H, 4.1%.

3) Synthesis of bis(acyl)phosphane oxide (BAPO) photoinitiators

The general synthesis of the different BAPOs is described in PCT/EP2013/070378 (WO 2014/053455), WO 2011/003772 and WO 2006/056541. For BAPO-1, see example 23 of WO 2014/053455, for BAPO-2, see example 12a of WO 2014/053455, for BAPO-3, see example 27 of WO 2014/053455. BAPO-4 was prepared using BAPO-2 and the protocol described in example 34 of WO 2011/003772 and BAPO-5 was prepared according to example 23 of WO 2014/053455, using polyethyleneglycol diacrylate Mn 6000 as starting material.

BAPO-6 is soluble in water and the synthesis was performed as described for Example 1 in patent WO 2006/056541 using 3-Bromopropyltrimethylammonium bromide in ethanol for the alkylation of bisenolate Na[P(COMes)2]$_x$DME} (step d).

4) Synthesis of bis(acyl)phosphane oxide (BAPO) photoinitiator Linked to Vanadate and Polymerization of MMA A bis(acyl)phosphane oxide functionalized with a siloxane group (BAPO-2) was linked to a lithium oxohydroxide vanadate Li$_x$H$_y$V$_3$O$_8$ (wherein 2<x+y<6.8 and 0<x<4 and 0.5<y<6) (described within US20130157138 A1) (FIG. 1).

Figure 2:
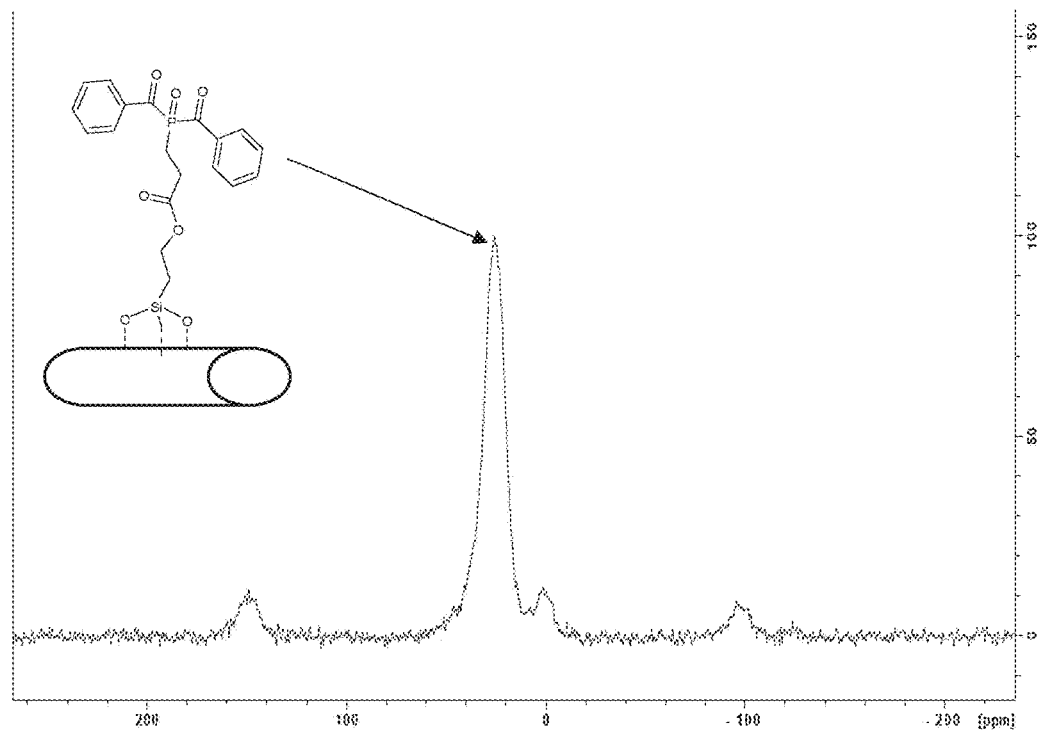
FIG. 2: $^{31}$P NMR of the photoinitiator linked to vanadate

The linking of the BAPO to the vanadate was carried out under argon atmosphere in a 100 mL Schlenk flask connected to a reflux condenser. To a suspension of Li$_x$H$_y$V$_3$O$_8$ (1 g) in THF (30 mL) was added BAPO-2 (0.05 g, 0.087 mmol) and the mixture refluxed during 4 h. After cooling down the mixture, the solid was filtered, washed, and sonicated two times for 1 min in THF (20 mL). The resulting greenish solid was dried under vacuum at 50° C. for 24 h affording 0.95 g. Analysis of the material was performed spectroscopically (MAS NMR) to confirm the presence of bis(acyl)phosphane)oxide photoactive group in the material ($^{31}$P NMR) (FIG. 2).

Figure 3:
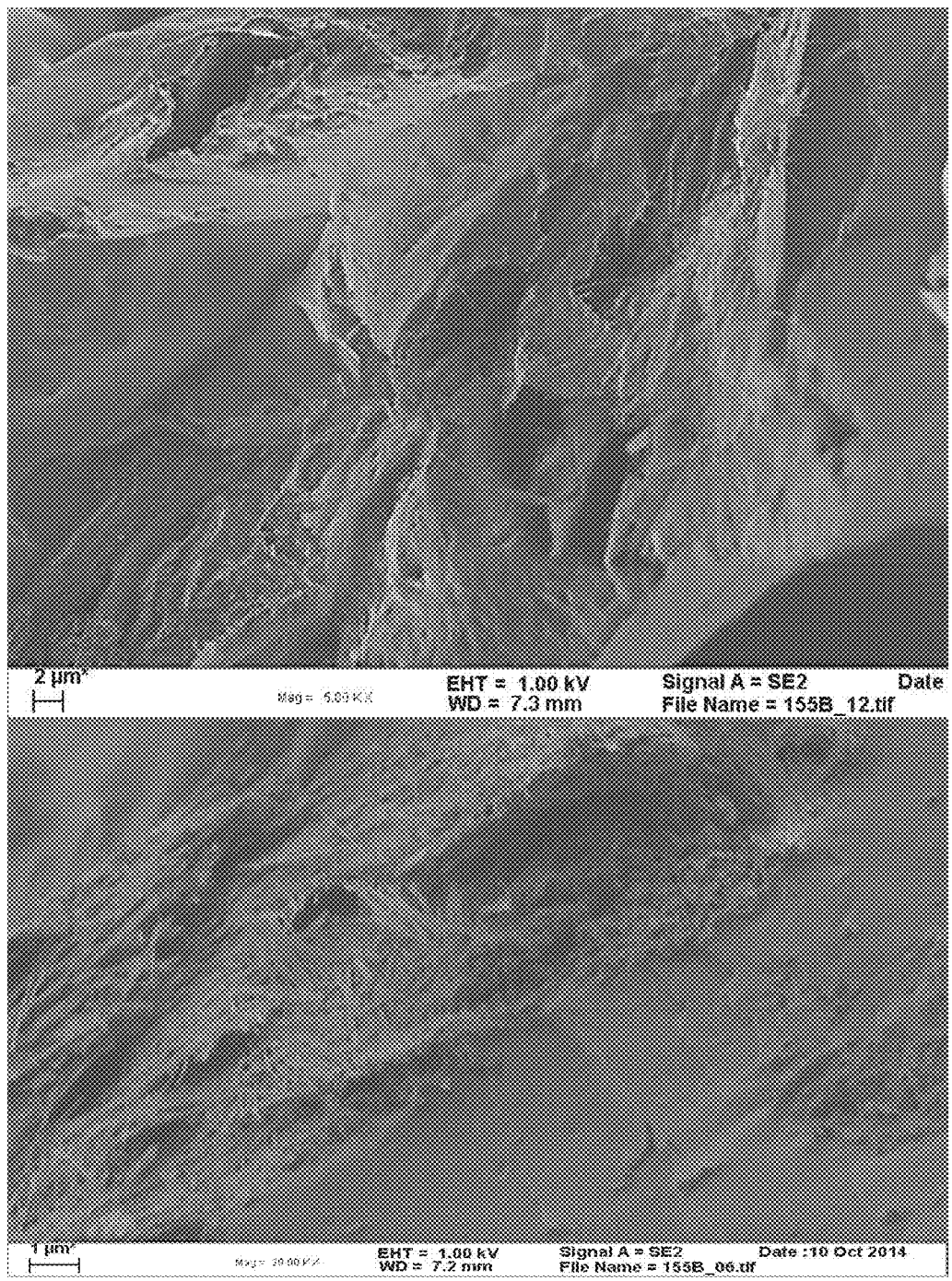
FIG. 3: SEM image of PMMA embedding the Li$_x$H$_y$V$_3$O$_8$ fibers resulted from a BAPO-vanadate polymerization

5) Synthesis of PMMA by Radical Polymerization Using a Vanadate Linked Photoinitiator The photoinitiated polymerization of MMA was carried out in a 100 mL Schlenk under argon atmosphere. A suspension of the linked photoinitiator (0.95 g) in THF (30 mL) was prepared and the MMA (0.78 g, 7.8 mmol) added to the suspension. The mixture was stirred vigorously for 5 min before irradiation. The irradiation of the mixture was performed with a mercury UV lamp under vigorous stirring at room temperature during 1 h affording a gel. The greenish solid was suspended in 50 mL of THF sonicated and filtered. The sample was dried under vacuum affording 0.87 g of a greenish solid. The morphology of this solid was investigated by SEM analysis (FIG. 3).

6) Synthesis of the Copolymers (CP-1 to CP-6)

6a) Synthesis of Tri-Block Copolymers (TBP-1 to TBP-5)

Reaction Path for the Synthesis of TBP-1:

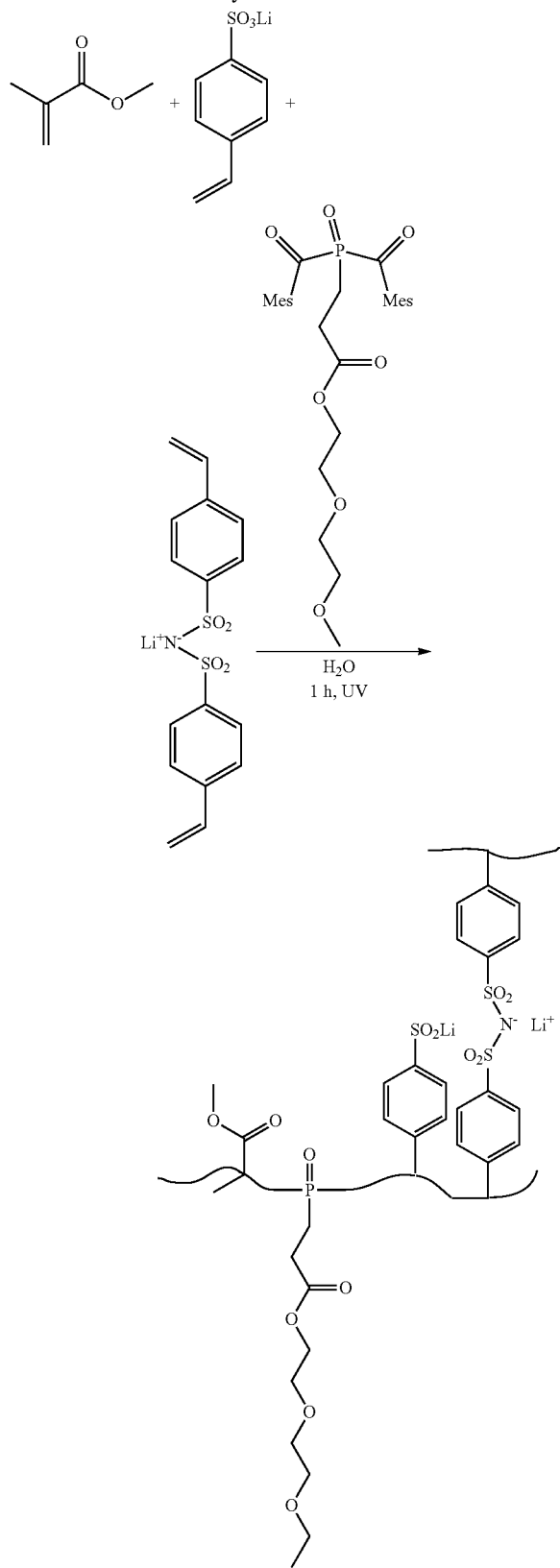

The synthesis of the polymer TBP-1 (1 b) was carried out in a 100 mL Schlenk flask under argon atmosphere. The reactor was charged with lithium sulfonate styrene (4 mmol, 760 mg), lithium bis(styrenesulfonyl)imide (0.8 mmol, 284 mg) and distilled water (30 mL). Freshly distilled methyl methacrylate (MMA) (4 mmol, 400 mg, 430 µL) and photoinitiator BAPO-1 (R=$CH_2CH_2CO(OCH_2CH_2)_2OEt$) (0.08 mmol, 42 mg) dissolved in DME (dimethoxyethane) (5 mL) were slowly added under argon atmosphere to the stirred mixture. To the reaction mixture lithium dodecylsulfate (9 mM) was added. The emulsion was deoxygenated for 20 min prior to being irradiated at 22° C. with a middle pressure mercury UV lamp (254 nm) for 1 h while maintaining a vigorous stirring (1200 rpm) resulting in a white suspension.

The polymer was isolated by removing solvent under vacuum (40 C.°, 20 mbar). The resulting white viscous residual was washed with isopropanol (2×5 mL) and tetrahydrofuran (2×5 mL). The recovered polymer was dried under vacuum overnight (25 C.°, 0.1 mbar) affording 945 mg (71% yield).

Stable suspensions of the polymer were prepared by adding distilled water and 5% (w/w) tetraethyleneglycol dimethylether (TEG). TEG was added as plasticizer to avoid dense packing of the polymer.

Synthesis of TBP-2 to TBP-5 was performed analogously.

6b) Synthesis of Polymer DBP-6

For polymer TBP-6 a preferential ratio of lithium styrylsulfonate to cross linker is a 10:1 ratio with no acrylate or methacrylate employed. Except for this change and the fact that the BAPO-6 was added to the aqueous solution containing monomers, the procedure for TBP-1 was followed.

7) Preparation of Self-Standing Films of SPE from the Suspension of the TBP

Self standing films of the polymer electrolyte were prepared by casting the TBP suspension within Teflon plates with 300-500 µm circular groves. These circular groves had the size of the electrolyte films required for conductivity and battery tests (Ø 15 and 17 mm). The polymers were initially dried at room temperature under Ar for 24 h; then at 50° C. under Ar during 4 days, and finally under vacuum at 50° C. for 24 h. The processing resulted in homogeneous self-standing films of 200-700 µm which were stored in a glove box for 2 days prior to use.

8) Characterization of Tri-Block Copolymers (TBP) (after Processing as Self-Standing Films)

8a) Methods Used

NMR

The MAS NMR experiments were performed using a Bruker Avance 400 MHz 9.4T spectrometer. The $^7$Li MAS NMR spectra were recorded at 155.50 MHz using 1.0 s radiofrequency pulses, a recycle delay of 2.0 s, a number of transient of 600, and a spinning rate of 7.0 kHz.

XRD

Powder X-ray diffraction patterns were obtained on a STOE Stadi P diffractometer equipped with a germanium monochromator and $CuK_\alpha1$ radiation (operated at 40 kV, 35 mA).

SEM

Scanning electron microscopy (SEM) was performed on a Zeiss Gemini 1530 operated at 1 kV.

TEM

Transmission electron microscopy (TEM) was performed on a CM30ST (FEI; LaB6 cathode) and a TecnaiF30 microscope that were operated at 300 kV with a maximum point resolution of ca. 2 Å.

Ionic Conductivity

Impedance measurements were carried out in the frequency range of 500 kHz to 1 Hz using an excitation amplitude of 50 mV (VMP3, Biologic SAS, France). Discs of 17 mm diameter were cut from the electrolyte film and the samples were placed between two round stainless steel discs (1.8 cm$^2$) and sealed for air and moisture protection with a temperature stable tape. From the obtained line the bulk resistance (R) was calculated selecting the minimum in the Nyquist plot between the electrolyte arc and the beginning of the interfacial arc. The bulk resistance R of the polymer is then used to calculate the conductivity ($\sigma$) according to Eq. 1, where d is the sample thickness and A the sample area measured between the steel discs. This methodology has been broadly described to measure the ionic conductivity of SPE at different temperatures.[11]

$$\sigma = \frac{d}{A*R} \qquad \text{Eq. 1}$$

8b. Characterization of Tri-Block Copolymer TBP-1

$^7$Li MAS NMR $\delta=-0.5$ ppm
ATR IR: $\upsilon(cm^{-1})$=2350 w, 1724 s, 1456 m, 1248 s, 1149 s, 1085 s, 1030 s, 985 m, 948 m, 892 m, 758 m, 638 s
EA C, 52.8%; H, 4.0%; N, 0.7%.

Figure 4:
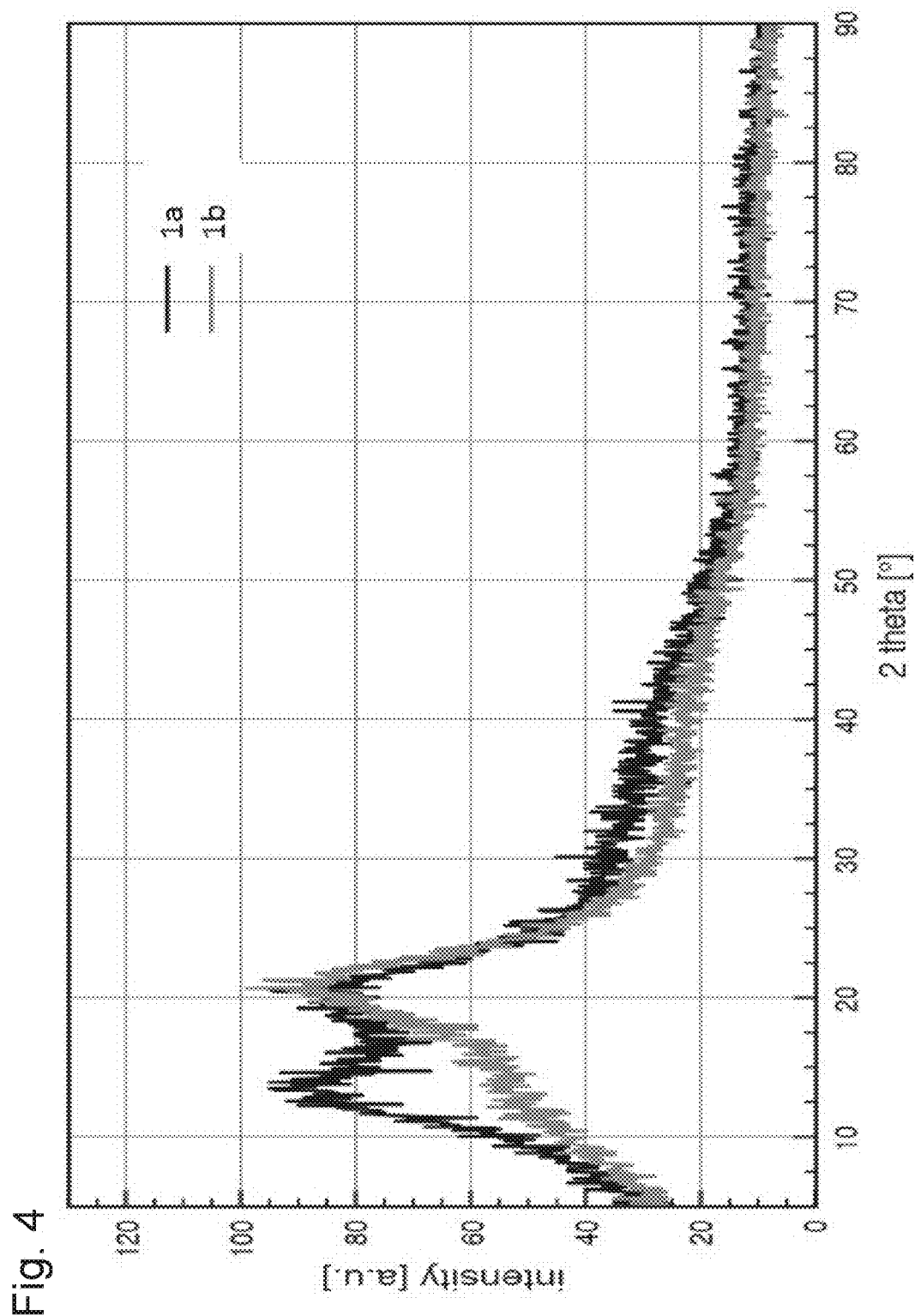
FIG. 4: XRD pattern of the films polymer TBP-1 1a (prepared without LiDS) and 1 b (with 9 mM LiDS)

Using XRD-diffraction no clear crystallinity was found for TBP1, independently on the addition of surfactant (LiDS). Only a very broad signal in the 2θ range of 10°-25° was detected, suggesting that the polymer contains regions having ordered chains, but from the signal width, it can be stated that these ordered domains are very small or not well defined (FIG. 4).

Figure 5:
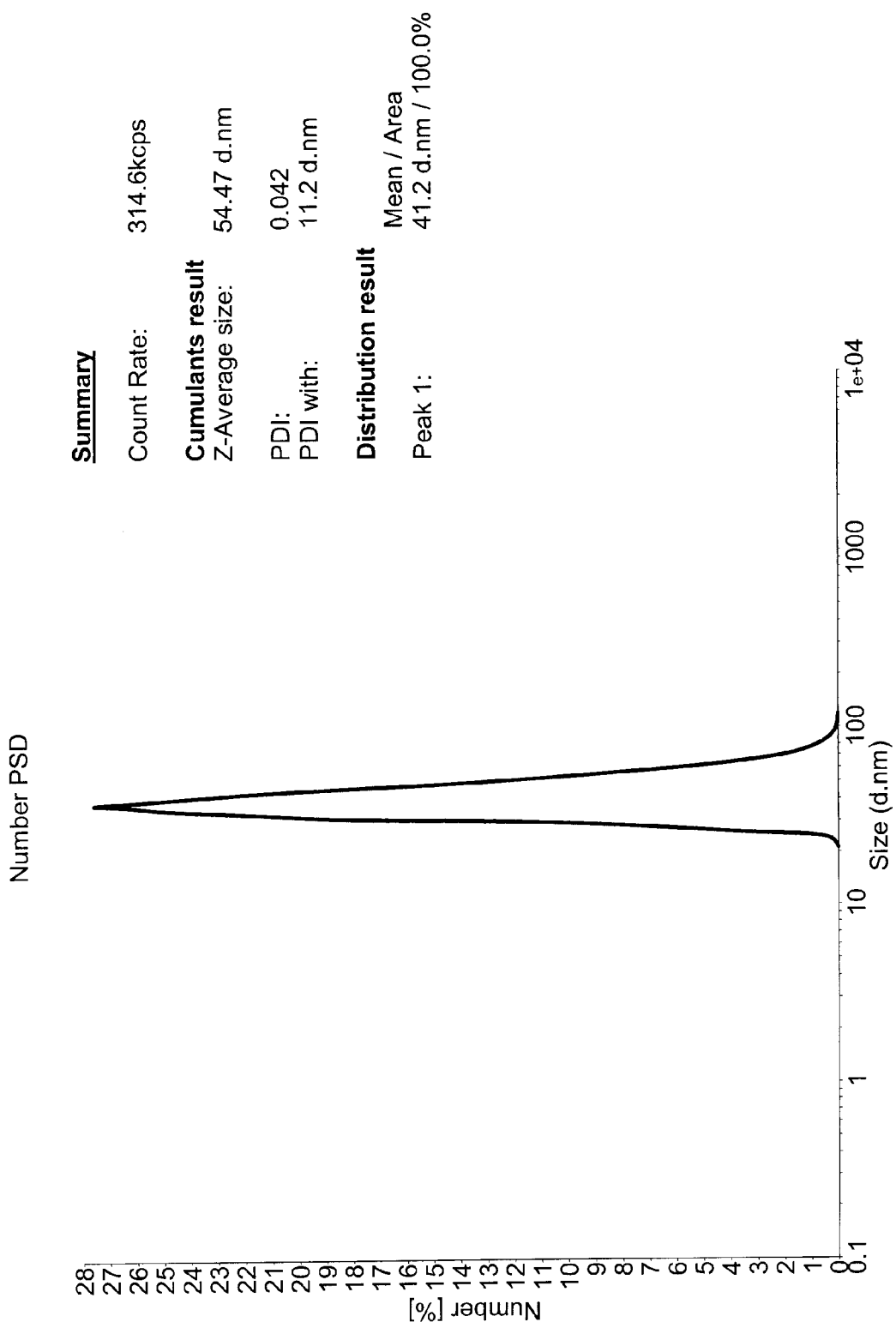
FIG. 5: Particle size distribution of polymer TBP-1 in water

On the other hand, the addition of LiDS had an influence on the polymer particle size and distribution. The polymer prepared without LiDS exhibited inferior stability and suffered from particle sedimentation after few hours. Zeta size measurements of polymer suspensions containing LiDS (9 mM) showed a narrow distribution of the particles size around 41 nm (FIG. 5). The size distribution remained unchanged after 2 weeks aging, and was used for the preparation of composite films.

Figure 6:
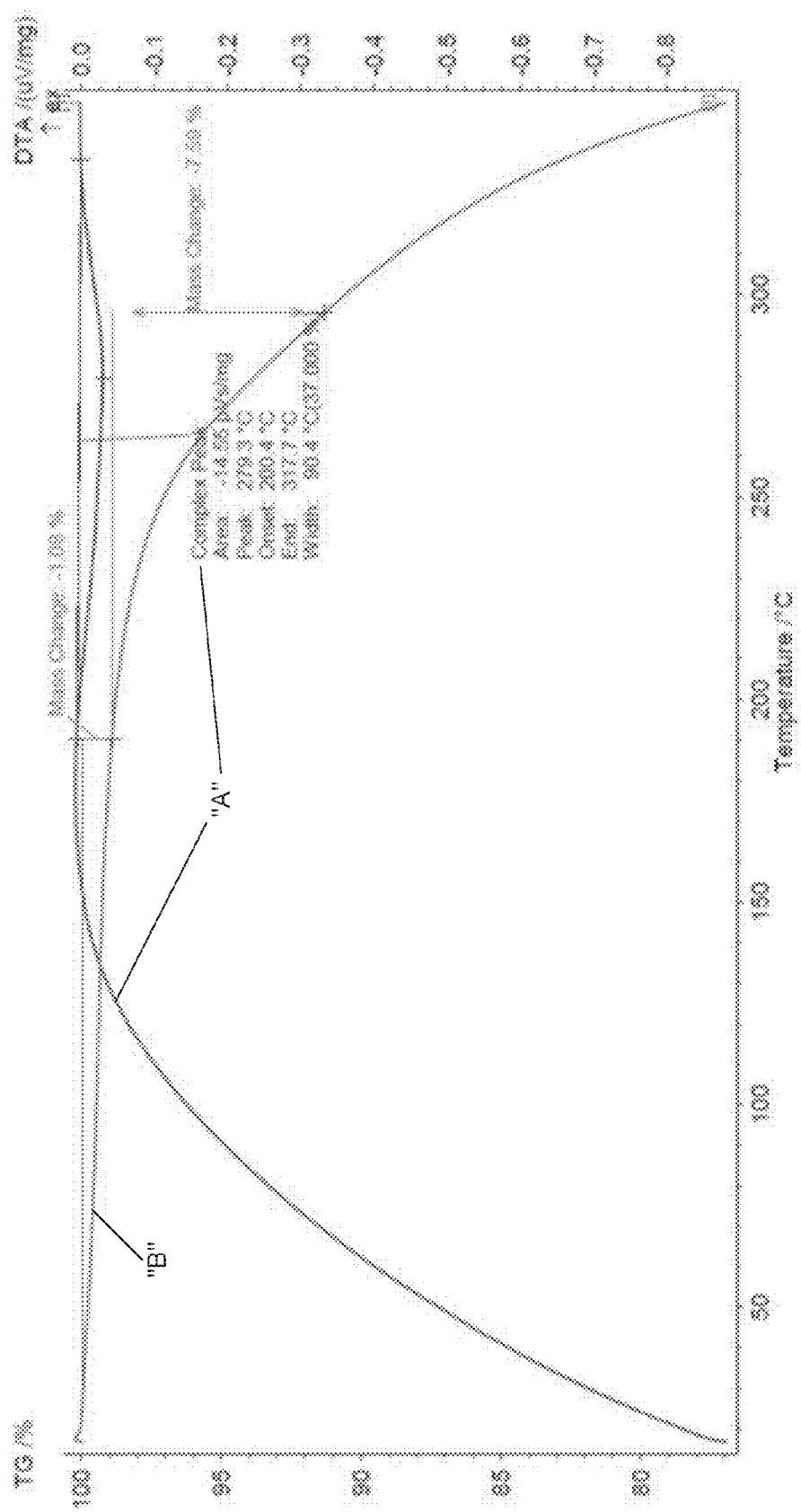
FIG. 6: TGA ("A") and DSC ("B") curves for TBP-1

The thermal stability of the polymers was evaluated by thermal gravimetric analysis (TGA). TBP1 was thermally stable up to 190° C., with negligible mass loss (1%). There was an increasing mass loss of 7.6% at 290° C. The melting behavior of the polymers was quantified using differential scanning calorimetry (DSC) and representative curves for the polymer 1a are represented in FIG. 6 showing an endothermic peak at 290° C.

Figure 7:
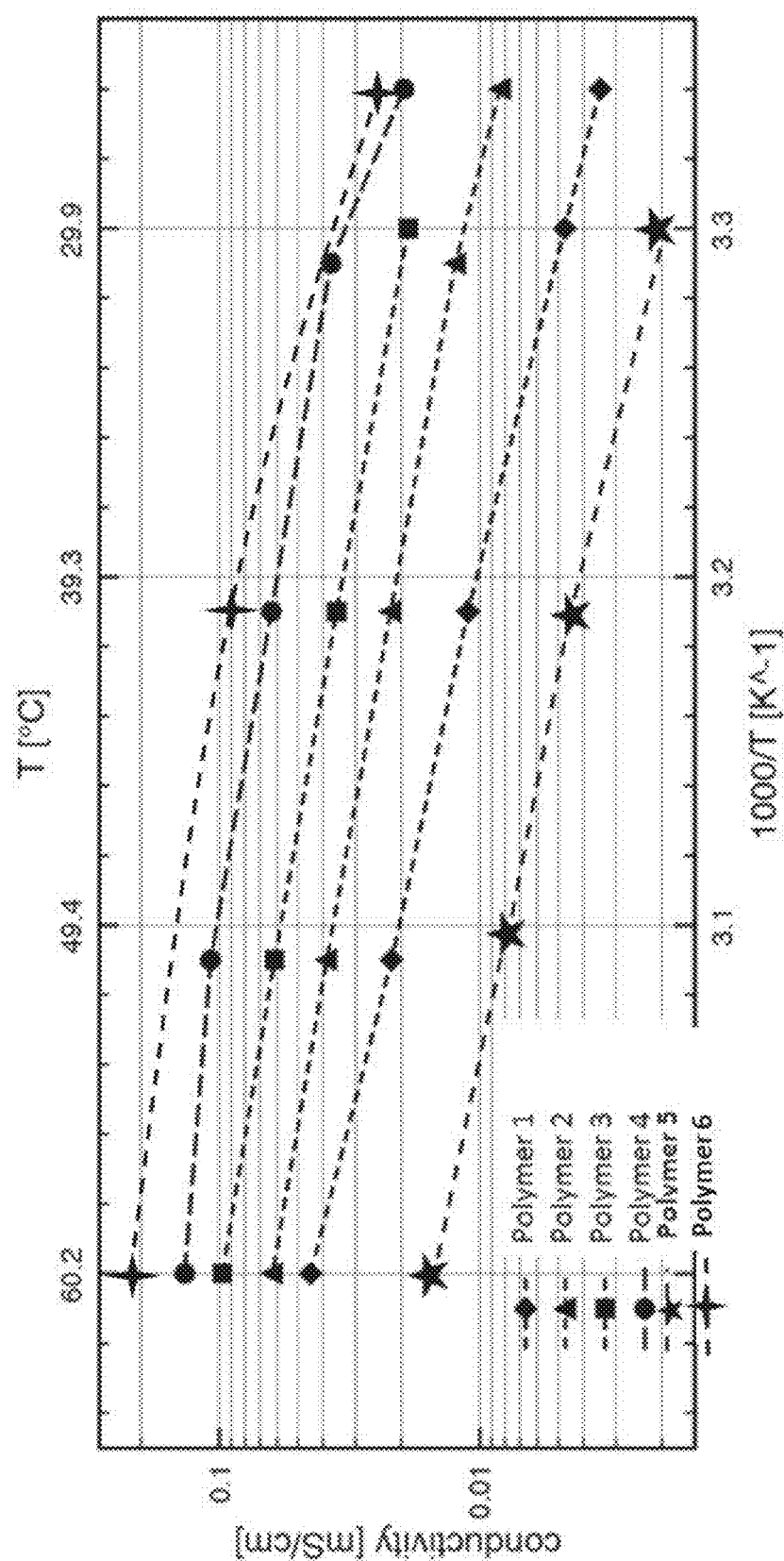
FIG. 7: Temperature dependence of conductivity (plotted logarithmically) for the tri-block polymers (TBP-1 to TBP-5 and DBP-6) prepared using the BAPO-1, BAPO-6 respectively as photo-initiators.
Figure 8:
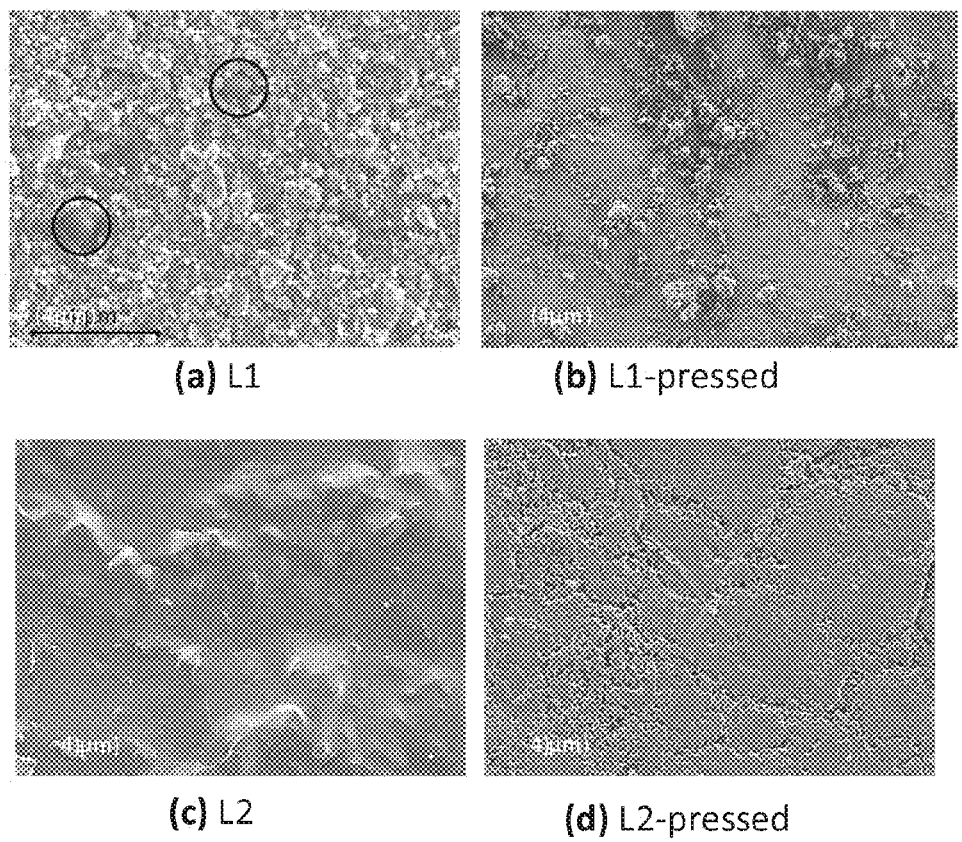
FIG. 8: SEM images of LFP composite cathode films (L1 and L2) before and after pressing

FIG. 7 shows the conductivity vs inverse of temperature (T$^{-1}$) for TBP-1 and the analogous polymers (TBP2, TBP3, TBP4, TBP5 and DBP6) prepared using the different BAPO photoinitiators described above. A linear increase in conductivity indicates that the conductivity mechanism remained the same throughout the temperature range measured. The maximum conductivity of 0.14 mS/cm at 60° C. was reached for the polymer obtained using a polymeric siloxane containing BAPO (BAPO-4). This sample however exhibited a deviation from the linear increase on the plot of logarithmic conductivity vs T$^{-1}$. This indicates a change of the conduction mechanism at higher temperature or the influence of a second conduction process. Chemical stability of the polymer films against lithium was tested by placing the film on freshly cut lithium in dry argon atmosphere. The interface polymer/Li remained unchanged after the polymer film was lifted in regular time intervals (up to 3 weeks).

9) Composite Cathode Preparation with TBP-1

9a) One step SPE/AM Composites Preparation

In a first step the cathode active materials (AM), either carbon coated lithium iron phosphate (LFP) (2 μm, A1100, Alees, Taiwan) or lithium oxohydroxide vanadate Li$_x$H$_y$V$_3$O$_8$ (wherein 2<x+y<6.8 and 0<x<4 and 0.5<y<6) (described in US20130157138 A1) were premixed with carbon black conductive additive (Super-P, Timcal) and alternatively also with graphite (SFG6 or KS6, Timcal, Switzerland) in an agate ball mill (300 rpm, 2×10 minutes). Then an aqueous suspension of the polymer TBP-1 with a concentration of 0.16 g/ml was added. Depending on the solid content, some additional de-ionized water was added until suitable viscosity of the slurry had been achieved. Optimal solid content around 18% and 35% for preparation of LFP and vanadates composites (L1-L2 and V1-V2) respectively were used. To prevent strong foaming during ball milling and resulting holes in the cathode films, a minimum amount of tributyl phosphate (>99.0%, Fluka Chemie AG, Buchs, Switzerland) was added as anti-foaming agent. After ball milling for 2×30 minutes (300 rpm, with reversed rotation direction) an homogenous slurry was obtained. The weight percent of different composite compositions are shown in Table 1.

TABLE 1

LFP or Li$_x$H$_y$V$_3$O$_8$ composites with different ratios.

| | LFP composite L1(%) | LFP composite L2(%) | Li$_x$H$_y$V$_3$O$_8$ V1(%) | Li$_x$H$_y$V$_3$O$_8$ V2(%) |
|---|---|---|---|---|
| AM = (LFP or Li$_x$H$_y$V$_3$O$_8$) | 74 | 55 | 46 | 43 |
| Graphite (SFG6) | 10 | 10 | 15 | 0 |
| Super P | 5 | 5 | 11 | 29 |
| Polymer TBP-1 | 11 | 30 | 27 | 27 |

Figure 9:
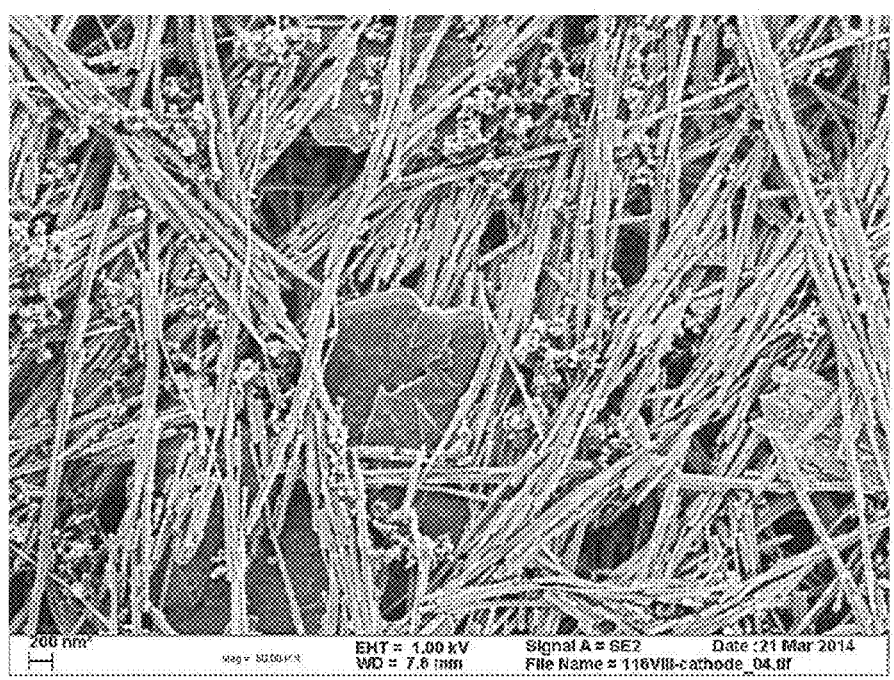
FIG. 9: SEM images of vanadate composite cathode films (V1)
Figure 10:
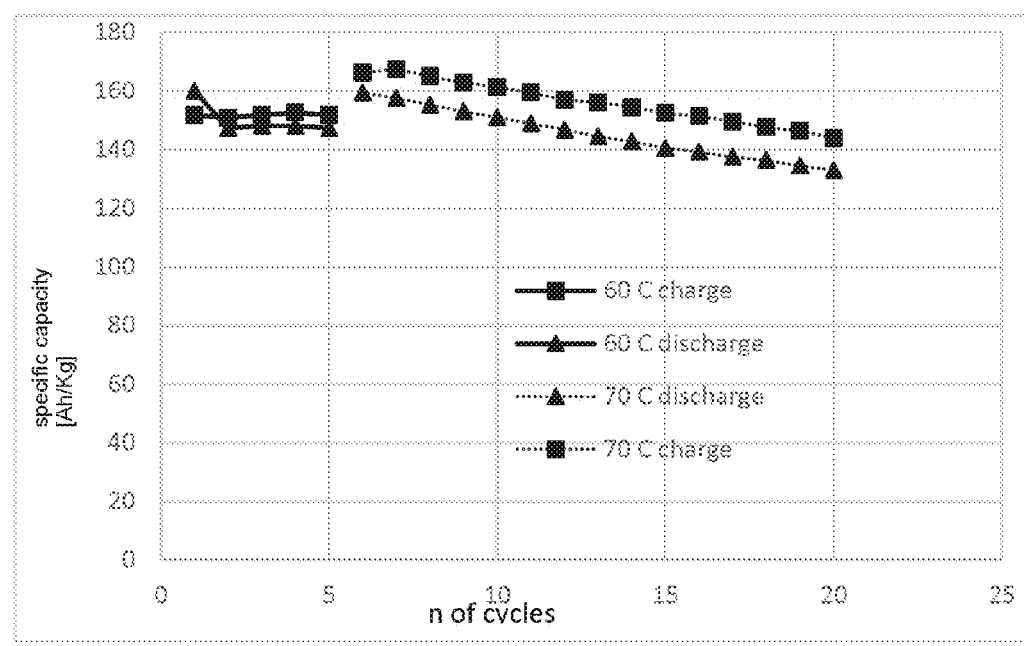
FIG. 10: Cycle-life of the composite L1 using the polymer TBP-1a at 60° C. and 70° C. with a current of 20 mA/g (C/8).

The slurries were casted by doctor-blading on standard aluminum foil (15 μm). The films were dried for one hour at room temperature and an airflow, then for 12 h at 50° C. under an Argon atmosphere, and finally for at least 24 h at 50° C. under vacuum, resulting in 40-100 μm thick dry films. The films were pressed (15 tons, 5 min) to reduce voids in the film and improve contact between particles. The microstructures of the LFP based films are shown in FIG. 9 and the corresponding microstructure of the vanadate based films in FIG. 10.

9b) Two Steps SPE/AM Composites Preparation by Coating and Infiltration

As an alternative way to prepare SPE/AM composites, a LFP-based cathode was first bar coated on an aluminum foil and then a SPE-solution was drop casted on the cathode.

The coated cathode had a composition of 88% (LFP), 6% (KS6) and 4% (SuperP)). In order to assure adhesion to the aluminum foil 2% of sodium methyl cellulose (Na-CMC) was used as binder. Then a suspension of TBP1 in water (30% wt) was drop casted on the LFP-cathode. The composites cathodes were initially dried at room temperature under Ar for 24 h then at 50° C. under Ar during 24 h, and finally under vacuum (10 mbar) at 50° C. for 24 h. The resulting cathode composites (composite L3) were 100 µm thick and contain a load of 17.6 mg polymer/$cm^2$ cathode film.

10) Battery Setup

Electrochemical performance was tested in standard coin cells (CR2025, Renata, Switzerland). Lithium metal disk was used as anode. Disks of 13 mm diameter were subsequently cut from the composite cathode films.

For the composites prepared by one step route (L1-L2 & V1-V2), a SPE disk (diameter 17 mm) from the self-standing SPE film TBP1 was placed between the anode and the cathode. The test cells were assembled in dry Ar atmosphere (<0.1 ppm $H_2O$; <0.1 ppm $O_2$). For galvanostatic experiments, a current of 20-25 mA/g was used (based on the active material). The LFP window potential was 3.0-3.9 V and for vanadium 1.6-4.2 V.

10a) Electrochemical Performance of LFP-Composites (One Step Synthesis)

The cathode L1 (FIG. 10) showed capacities close to the theoretical value (152 Ah/kg in the first cycle at 60° C.), and was stable for the five cycles measured at this temperature when cycled with a current of 20 mA/g (C/8). After these five cycles, the cell was transferred to another measurement device for long term measurement and the temperature was increased to 70° C. At this temperature, the capacity first increases to 167 Ah/kg. After 20 cycles 144 Ah/kg were measured.

10b) Electrochemical Performance of LFP-Composites (Two Step Synthesis)

Figure 11:
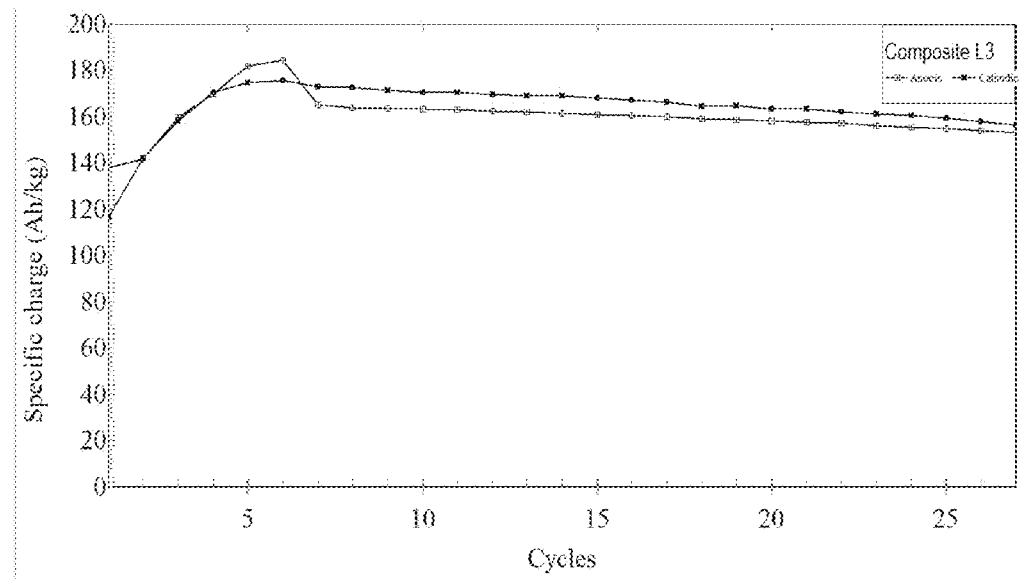
FIG. 11: Specific charge vs. cycle for composite L3

In FIG. 11 the composite L3 (where the SPE was drop-casted, see 8b) had been galvanostatically cycled at 70° C. in the 3.0-3.9 V range with a current of 20 mA/g. In the first 6 cycles a slight overcapacity was observed and from the 7th cycle recharge efficiencies close to 100%. At C/8 rate, the performance of the cell still achieved capacities higher than 160 mA/g after the $20^{th}$ cycle.

10c) Electrochemical Performance of Vanadate-Composites (One Step Synthesis)

Figure 12:
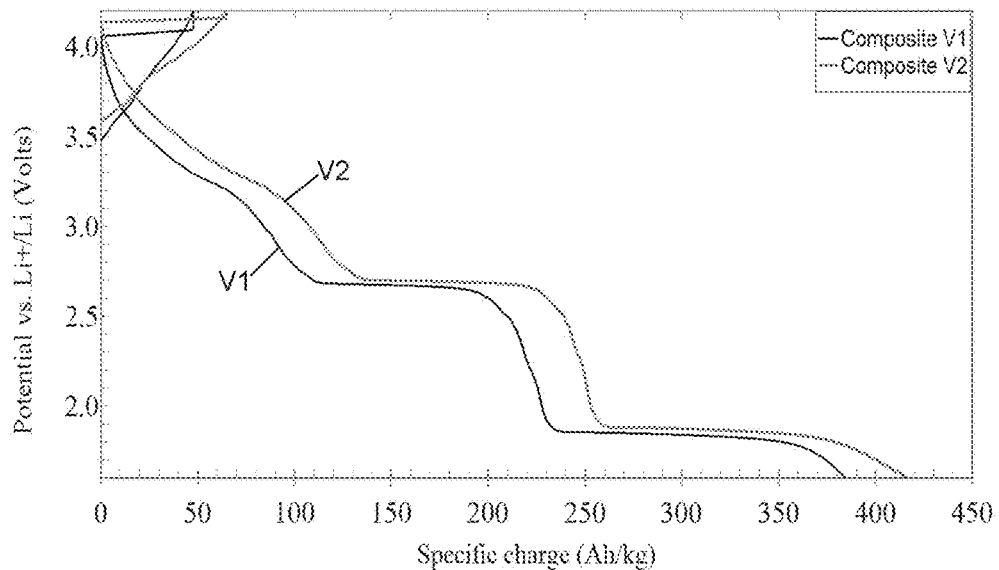
FIG. 12: Potential vs. specific charge for composite V1 and V2
Figure 13:
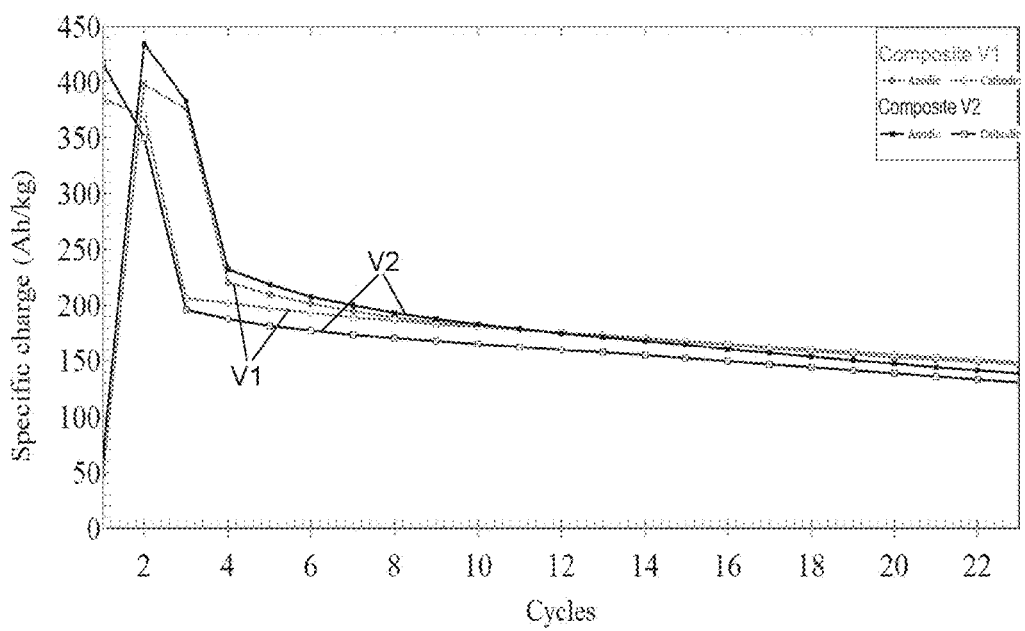
FIG. 13: Specific charge vs. cycle for composite V1 and V2.

FIG. 12 displays the potential vs $Li^+$/Li (V) versus specific charge (Ah/Kg) for the first cycles of batteries using cathode V1 and V2 at 70° C. In FIG. 13, the capacity in dependence on the cycle number is shown for both composites up to the $23^{th}$ cycle. The cathode composite V1 exhibited capacities in the first cycle of 398 Ah/kg close to the theoretical value, which decreased to 148 Ah/Kg after the 23th cycle. The cathode composite V2 achieved capacities up to 419 Ah/kg in the first cycle, which slowly decreased to 150 Ah/Kg after the 23th cycle. Remarkably, the columbic efficiency of composite V2 (Super P and graphite) was improved when compared to V2 (only SuperP as carbon additive).

While there are shown and described presently preferred embodiments of the invention, it is to be distinctly understood that the invention is not limited thereto but may be otherwise variously embodied and practiced within the scope of the following claims.

REFERENCES

[1] Tollefson, J. Car industry: Charging up the future. *Nature* 2008, 456, 436.

[2] a) Cheng, F., Liang, J., Tao, Z. & Chen, J. Functional materials for rechargeable batteries. *Adv. Mater.* 2011, 23, 1695.

b) Armand, M. & Tarascon, J-M. Building better batteries. *Nature* 2008, 451, 652.

[3] Bruce, P. G., Freunberger, S. A., Hardwick, L. J. & Tarascon, J-M. LiO2 and Li2S batteries with high energy storage. *Nature Mater.* 2012, 11, 19.

[4] Hammami, A., Raymond, N. & Armand, M. Lithium-ion batteries: Runaway risk of forming toxic compounds. *Nature* 2003, 424, 635.

[5] Murata, K., Izuchi, S. & Yoshihisa, Y. An overview of the research and development of solid polymer electrolyte batteries. *Electrochim. Acta* 2000, 45, 1501.

[6] Bruce, P. G. & Vincent, C. A. Polymer electrolytes. *J. Chem. Soc. Faraday Trans.* 1993, 89, 3187.

[7] Marzantowicz, M., Dygas, J. R., Krok, F., Florjaczyk, Z. & Zygad Monikowska, E. Influence of crystalline complexes on electrical properties of PEO:LiTFSI electrolyte. *Electrochim. Acta* 2007, 53, 1518.

[8] a) Vaia, R. A., Vasudevan, S., Krawiec, W., Scanlon, L. G. & Giannelis, E. P. New polymer electrolyte nanocomposites: Melt intercalation of poly(ethylene oxide) in mica-type silicates. *Adv. Mater.* 1995, 7, 154.

b) Wong, S. & Zax, D. B. What do NMR linewidths tell us? Dynamics of alkali cations in a PEO-based nanocomposite polymer electrolyte. *Electrochim. Acta.* 1997, 42, 3513.

c) Bujdàk, J., Hackett, E. & Giannelis, E. P. Effect of layer charge on the intercalation of poly(ethylene oxide) in layered silicates: Implications on nanocomposite polymer electrolytes. *Chem. Mater.* 2000, 12, 2168.

d) Capiglia, C., Mustarelli, P., Quartarone, E., Tomasi, C. & Magistris, A. Effects of nanoscale SiO2 on the thermal and transport properties of solvent-free, poly(ethylene oxide) (PEO)-based polymer electrolytes. *Solid State Ion.* 1999, 118, 73.

e) Croce, F., Appetecchi, G. B., Persi, L. & Scrosati, B. Nanocomposite polymer electrolytes for lithium batteries. *Nature* 1998, 394, 456.

f) Forsyth, M. et al. The effect of nano-particle TiO2 fillers on structure and transport in polymer electrolytes. *Solid State Ion.* 2002, 147, 203.

[9] Aryanfar, A., rooks, P., Merinov, B. V., Goddard, W. A., Colussi, A. J., Hoffmann, M. R., *J. Phys. Chem. Lett.* 2014, 5, 1721.

[10] Bonnet J. P., Bouchet, R., Aboulaich, A., Gigmes, D. Maria, S., Bertin, D., Armand, M. Phan, T., Meziani, R. Block copolymer including a polyanion based on a TFSI anion monomers: A battery electrolyte. WO2013034848.

[11] Murata, K., Izuchi, S. & Yoshihisa, Y. An overview of the research and development of solid polymer electrolyte batteries. *Electrochim. Acta* 2000, 45, 1501.

What is claimed is:

1. A method for the production of a solid conducting polymer, comprising:
copolymerizing a monomer mixture comprising a bis(styrylsulfonylimide) salt of formula (I) to form the solid conducting polymer having crosslinking units of the bis(styrylsulfonylimide) salt,

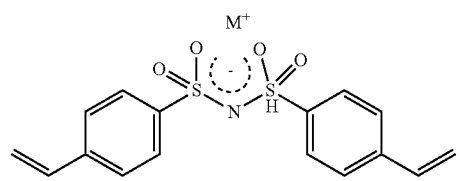

wherein M⁺ is Li⁺ or Na⁺, as cross linking monomer, with an alkaline metal vinyl sulfonate monomer and a radical initiator, wherein the radical initiator is selected from the group consisting of a photoinitiator, a thermal initiator and combinations thereof.

2. A method for the production of a solid polymer electrolyte, comprising:
copolymerizing a monomer mixture comprising a bis(styrylsulfonylimide) salt of formula (I) to form a solid conducting polymer having crosslinking units of the bis(styrylsulfonylimide) salt,

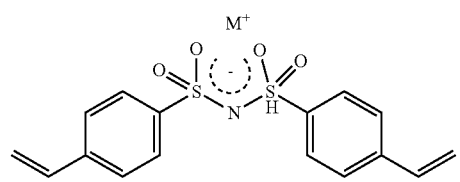

wherein M⁺ is Li⁺ or Na⁺, and
forming the solid polymer electrolyte from the solid conducting polymer, as cross linking monomer, with an alkaline metal vinyl sulfonate monomer and a radical initiator, wherein the radical initiator is selected from the group consisting of a photoinitiator, a thermal initiator and combinations thereof.

3. A solid single-ion conducting polymer produced by copolymerizing a bis(styrylsulfonylimide) salt of formula (I) as a cross linking monomer, with an alkaline metal vinyl sulfonate monomer and a radical initiator, wherein said radical initiator is selected from the group consisting of a photoinitiator, a thermal initiator and combinations thereof

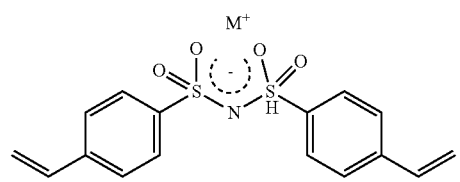

wherein M⁺ is Li⁺ or Na⁺.

4. The solid single-ion conducting polymer of claim 3, wherein it is a solid polymer electrolyte.

5. The solid single-ion conducting polymer of claim 3, wherein the solid single-ion conducting polymer further comprises copolymerized units of an acrylate monomer.

6. The solid single-ion conducting polymer of claim 5, wherein said acrylate monomer is a methacrylate monomer.

7. The solid single-ion conducting polymer of claim 6, wherein said acrylate monomer is methylmethacrylate.

8. The solid single-ion conducting polymer of claim 3, wherein the vinyl sulfonate monomer is styrene sulfonic acid salt.

9. The solid single-ion conducting polymer of claim 3, wherein the radical initiator is a photoinitiator or a combination of photoinitiator with a thermal initiator.

10. The solid single-ion conducting polymer of claim 3, wherein the radical initiator comprises a photoinitiator selected from the group consisting of an α-hydroxyketone, a benzophenone, a benzil derivative, a thioxanthone, an acetylphosphane, an alkoxyamine and an alkoxyamine.

11. The solid single-ion conducting polymer of claim 10, wherein the photoinitiator contains a photoinitiator of the acylphosphane oxide type of formula (II)

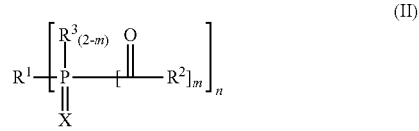

wherein
n is from 1 to 6,
m is 1 or 2,
X is oxygen or sulfur,
R¹ is —C(R⁴)₃, wherein
if n=1,
all R⁴ are independently from each other selected from the group consisting of
H,
aromatic groups,
alkenyl groups and
aliphatic groups, wherein the aliphatic groups can be unbranched or branched, non-substituted or substituted by one or more of the following groups: aromatic groups, heteroaromatic groups, heterocyclic groups, ethers (polyethyleneglycol or polyethylene oxide), selenides, hydroxyl, thiol, ketones, imines, carboxylic acid derivatives, sulfones, sulfoxides, sulfates, sulfonium, sulfimines, sulfoximine, sulfonamide, amine, ammonium salts, nitriles, nitro, amidines, carbamates, guanidinium, hydrazones, hydrazides, hydrazines, silanes, siloxanes, polysiloxanes, phosphonium, phosphinates, phosphine oxide or phosphate groups,
if n>1,
at least one R⁴ is a 2 to 6-valent substituent selected from the list described above, wherein the aforementioned alkyl can also comprise one, two or more of the afore mentioned groups within the chain, or be substituted once or more times with such groups, and wherein said groups are separated by at least one CH₂-group
R² is an aryl group, and
R³ is —C(R⁴)₃ as specified above for R¹.

12. The solid single-ion conducting polymer of claim 11, wherein n is 1, 2, 3 or 4.

13. The solid single-ion conducting polymer of claim 12, wherein n is 1 or 2.

14. The solid single-ion conducting polymer of claim 11, wherein $R^2$ is 2,4,6-trimethylphenyl (mesityl).

15. The solid single-ion conducting polymer of claim 11, wherein $R^2$ is 2,6-dimethoxyphenyl.

16. The solid single-ion conducting polymer of claim 11, wherein the photoinitiator is suitable to generate two radicals.

17. The solid single-ion conducting polymer of claim 11, wherein the photoinitiator is of formula (II) and wherein n is 1, m is 2, X is O, $R^1$ is —CH$_2$—CH$_2$(Z), Z is —(CH$_2$)$_{n1}$—NMe$_3$X'$^+$, wherein n$_1$ is from 1 to 4, and X' is Cl, Br, or I Z is an ester —(CO)OR$^6$ wherein R$^6$ is an alkyl comprising within its chain or said alkyl chain being interrupted by one or more —O—, or carrying one or more siloxy groups, or carrying one or more ammonium salt groups, and $R^2$ is a mesityl group or a 2,6-dimethoxyphenyl group, or n is 2, m is 2, $R^1$ is —(CO)O—(CH$_2$—CH$_2$—O)$_x$—O(CO)— wherein x is in the range of 1 to 1000, $R^2$ is a mesityl group or a 2,6-dimethoxyphenyl group.

18. The solid single-ion conducting polymer of claim 17, wherein n$_1$ is from 1 to 3.

19. The solid single-ion conducting polymer of claim 17, wherein R$^7$, R$^8$ and R$^9$ are C1 to C4 alkyl groups.

20. The solid single-ion conducting polymer of claim 17, wherein $R^2$ is a mesityl group.

21. The solid single-ion conducting polymer of claim 17, wherein x is from 1 to 100.

22. The solid single-ion conducting polymer of claim 11, wherein the photoinitiator is one of

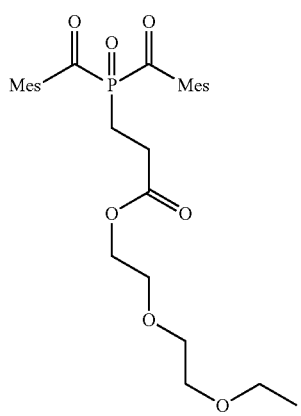

BAPO-1

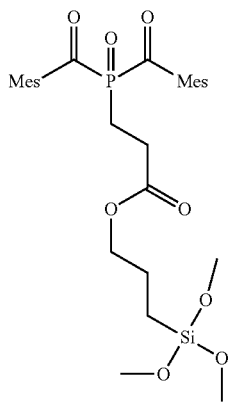

BAPO-2

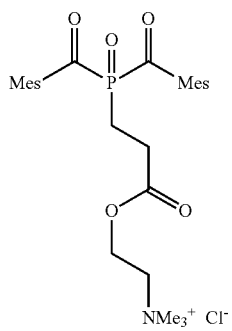

BAPO-3

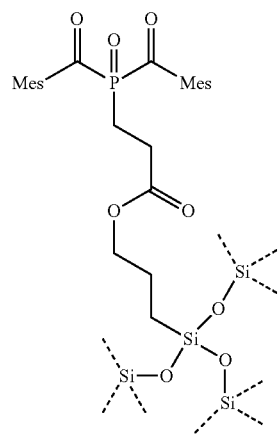

BAPO-4

Mn 2136

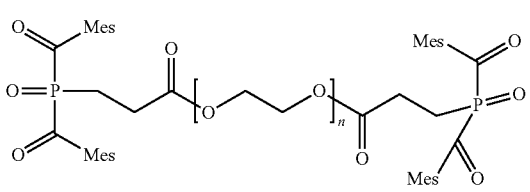

BAPO 5

Mn 6000
n = 100

-continued

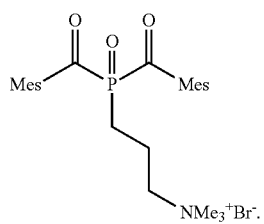

BAPO-6

23. The solid single-ion conducting polymer of claim 8, wherein the ratio of alkaline metal styrylsulfonate:acrylate is from about 1:0 to about 1:4.

24. The solid single-ion conducting polymer of claim 23, wherein the ratio of alkaline metal styrylsulfonate:acrylate is 1:1.

25. The solid single-ion conducting polymer of claim 5, wherein the cross linking monomer is present in a ratio of up to 20 mole-% referred to the amount of acrylate and sulfonate monomers.

26. The solid single-ion conducting polymer of claim 11, wherein $R^1$ is an alkyl group substituted by an ester group and wherein the ratio of acrylate:alkaline metal styrylsulfonate:cross-linking monomer is about 1:1:0.2 or wherein $R^1$ is an aliphatic group substituted by an ammonium salt and wherein the ratio of acrylate:alkaline metal styrylsulfonate:cross-linking monomer is about 0:10:1.

27. The solid single-ion conducting polymer of claim 3, wherein the photoinitiator and/or the thermally induced initiator is present in an amount of about 1 mol % of total monomers.

28. A battery comprising an electrolyte in which the electrolyte comprises the solid single-ion conducting polymer of claim 3, and the battery is a lithium ion battery or a sodium ion battery.

29. A battery comprising the solid single-ion conducting polymer of claim 3 as an electrolyte.

30. A cathode or an anode wherein the solid single-ion conducting polymer of claim 3 is intimately mixed with a cathode or anode electroactive material and optionally graphene and/or conductive carbon or graphite.

31. A method for producing the battery according to claim 29, comprising
    coating a releasable support with an active electrode material and optionally one or more conductive fillers to form a cathode and then coating the cathode with the solid single-ion conducting polymer.

32. The solid single-ion conducting polymer of claim 17, wherein $R^6$ is an alkyl comprising one or more siloxy groups bonded to a vanadate.

33. The solid single-ion conducting polymer of claim 17, wherein $R^6$ comprises a plurality of polyethylene groups interrupted by one or more —O—, or one or more siloxy groups of formula —$SiR^7_y(OR^8)_{3-y}$, wherein y is 0 from 3, or carrying one or more ammonium salt groups of formula —$N(R^9)^{4+}X'^-$ wherein $R^7$, $R^8$ and $R^9$ are alkyl groups.

34. A cathode or an anode wherein the solid single-ion conducting polymer of claim 3 is anchored to a cathode or anode electroactive material.

* * * * *

UNITED STATES PATENT AND TRADEMARK OFFICE
CERTIFICATE OF CORRECTION

PATENT NO. : 9,771,319 B2
APPLICATION NO. : 14/955264
DATED : September 26, 2017
INVENTOR(S) : Jose Antonio Gonzalez Martinez et al.

Page 1 of 2

It is certified that error appears in the above-identified patent and that said Letters Patent is hereby corrected as shown below:

In the Specification

Column 2, starting at Line 35, Formula (I) should read

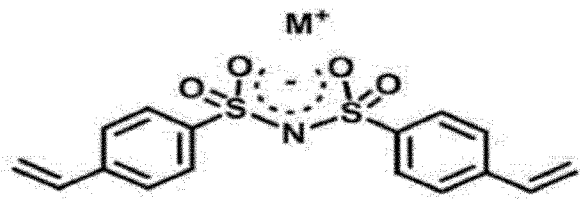

Column 9, Lines 62 and 63; Figs. 1 & 2 insert --.-- at the end of sentence

Columns 9 and 10, Lines 65, 67, 2, 3, 9, 11, 16; Figs 3, 4, 5, 6, 8, 9, 11, and 12 insert --.-- at the end of sentence.

In the Claims

Column 19, Formula (I) should read

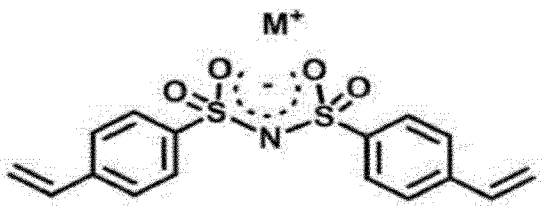

Signed and Sealed this
Fourteenth Day of May, 2019

Andrei Iancu
*Director of the United States Patent and Trademark Office*

CERTIFICATE OF CORRECTION (continued)
U.S. Pat. No. 9,771,319 B2

Column 19, Claim 2, Formula (I) should read

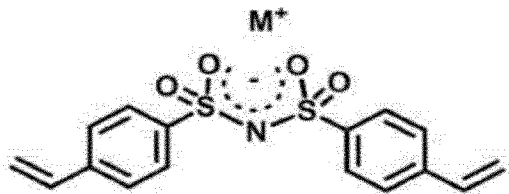

Column 19, Claim 3, Formula (I) should read

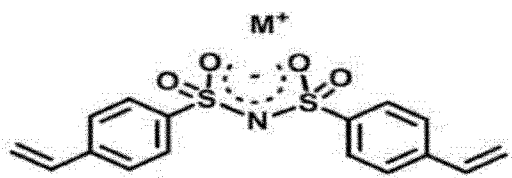

Column 20, Claim 11, Line 60 afore mentioned should read aforementioned

Column 23, Claim 26, Lines 25 and 28 cross-linking should read crosslinking